US010632461B2

(12) United States Patent
Kushima et al.

(10) Patent No.: US 10,632,461 B2
(45) Date of Patent: Apr. 28, 2020

(54) CHEMICAL CONTAINER

(71) Applicant: Toshiba Medical Systems Corporation, Otawara-shi (JP)

(72) Inventors: Hiroaki Kushima, Otawara (JP);
Nobuo Kawamura, Nasushiobara (JP);
Tetsuya Kuwabara, Nasushiobara (JP);
Sotaro Taki, Utsunomiya (JP)

(73) Assignee: Canon Medical Systems Corporation, Otawara-shi (JP)

( * ) Notice: Subject to any disclaimer, the term of this patent is extended or adjusted under 35 U.S.C. 154(b) by 67 days.

(21) Appl. No.: 15/718,698

(22) Filed: Sep. 28, 2017

(65) Prior Publication Data
US 2018/0093264 A1 Apr. 5, 2018

(30) Foreign Application Priority Data

Sep. 30, 2016 (JP) ................................. 2016-193602
Sep. 22, 2017 (JP) ................................. 2017-182941

(51) Int. Cl.
B01L 3/00 (2006.01)
C12N 15/10 (2006.01)
B65D 81/32 (2006.01)

(52) U.S. Cl.
CPC ............. *B01L 3/5023* (2013.01); *B01L 3/523* (2013.01); *B65D 81/3266* (2013.01);
(Continued)

(58) Field of Classification Search
CPC .. B01L 3/5023; B01L 3/523; B01L 2300/069;
B01L 2400/0683;
(Continued)

(56) References Cited

U.S. PATENT DOCUMENTS 3,539,505 A * 11/1970 Lauer ..................... B01D 15/22
210/656
5,882,495 A * 3/1999 Garrels ............ G01N 27/44704
204/456
(Continued)

FOREIGN PATENT DOCUMENTS

JP 2007-209705 * 8/2007 ................ A61J 1/05
JP 4366131 11/2009
(Continued)

OTHER PUBLICATIONS

Derwent Translated Abstract of Foreign Document JP 2007-209705;
Yoshikawa, Kazunari, Aug. 2007. (Year: 2007).*

Primary Examiner — Joseph W Drodge
(74) Attorney, Agent, or Firm — Oblon, McClelland, Maier & Neustadt, L.L.P.

(57) ABSTRACT

According to one embodiment, a sealed chemical container has a bonding area where a flexible sheet-like member is firmly bonded onto a plate, and the bonding area defines a first compartment which can be swollen and an outflow passage which communicates with the first compartment via an opening. A first seal portion is weakly bonded onto the plate compared to the bonding area to define the first compartment to block communication between the first compartment and an outflow passage. The first seal portion is peeled off by an increase in internal pressure in the first compartment to allow communication between the first compartment and the outflow passage.

28 Claims, 19 Drawing Sheets

(52) U.S. Cl.
CPC .... *C12N 15/1003* (2013.01); *B01L 2300/069* (2013.01); *B01L 2300/087* (2013.01); *B01L 2300/0816* (2013.01); *B01L 2300/0867* (2013.01); *B01L 2300/0887* (2013.01); *B01L 2400/0481* (2013.01); *B01L 2400/0683* (2013.01); *B01L 2400/0694* (2013.01)

(58) Field of Classification Search
CPC ..... B01L 2300/0867; B01L 2400/0481; B01L 2300/087; B01L 2300/0887; B01L 2400/0694; B01L 2300/0816; B01L 3/502; B01L 2300/04; B01L 2300/0861; B01L 2300/0877; B01L 2300/14; B01L 2400/0475; B65D 81/3266; B65D 81/3261; C12N 15/1003
USPC ..... 210/502.1, 638; 220/501, 502, 523, 524, 220/526, 529, 530; 422/417, 420, 501, 422/503, 504, 516, 547, 551, 552; 435/6.1, 6.19, 287.2, 287.3, 287.6, 287.7, 435/288.3, 288.4, 288.5
See application file for complete search history.

(56) References Cited

U.S. PATENT DOCUMENTS

| | | | |
|---|---|---|---|
| 6,485,690 B1* | 11/2002 | Pfost | B01J 19/0046 422/552 |
| 6,585,939 B1* | 7/2003 | Dapprich | B01L 3/502707 264/239 |
| 6,699,665 B1* | 3/2004 | Kim | B01L 3/5025 435/288.4 |
| 7,736,594 B1* | 6/2010 | Grudzien | B01L 3/50855 422/417 |
| 8,293,519 B2* | 10/2012 | Xian | B01L 3/50853 422/501 |
| 2003/0026739 A1* | 2/2003 | MacBeath | B01J 19/0046 422/417 |
| 2006/0029955 A1* | 2/2006 | Guia | G01N 33/48728 435/6.11 |
| 2008/0029451 A1* | 2/2008 | Chisholm | B01D 63/082 210/459 |
| 2012/0264650 A1* | 10/2012 | Luckey | B01L 3/5085 506/16 |
| 2013/0294982 A1* | 11/2013 | Takahashi | B01L 3/56 422/503 |
| 2015/0276089 A1* | 10/2015 | Unger | B01L 3/502707 137/823 |

FOREIGN PATENT DOCUMENTS

| | | |
|---|---|---|
| JP | 2011-509218 | 3/2011 |
| JP | 5021323 | 9/2012 |
| JP | 2015-529085 | 10/2015 |
| WO | WO 2009/086300 A1 | 7/2009 |

* cited by examiner

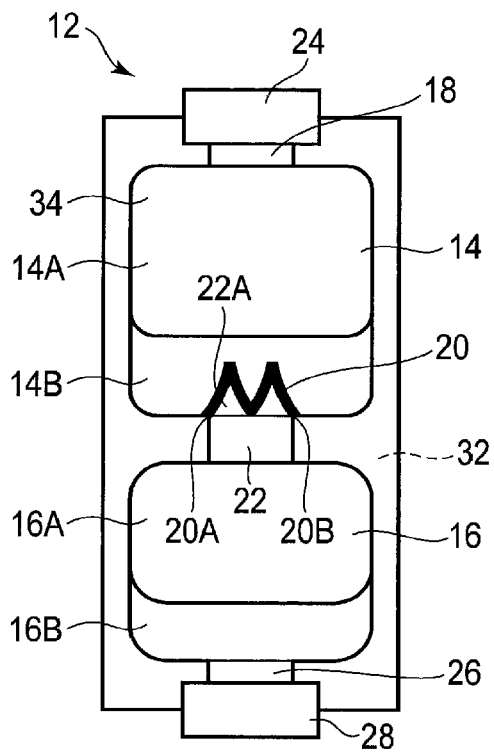
F I G. 8
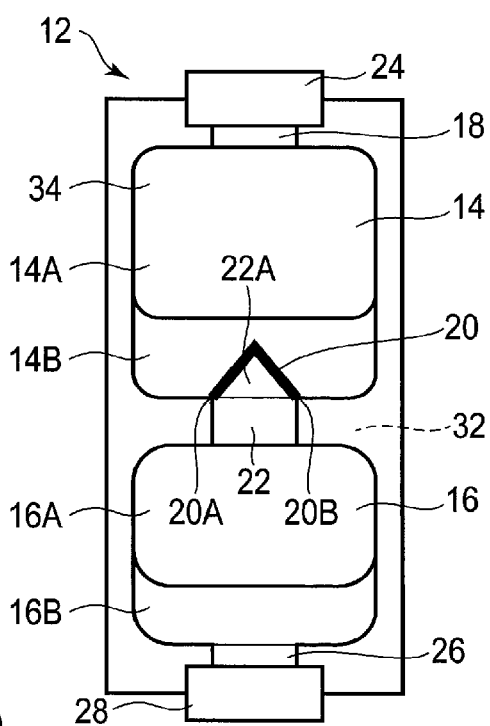
F I G. 9

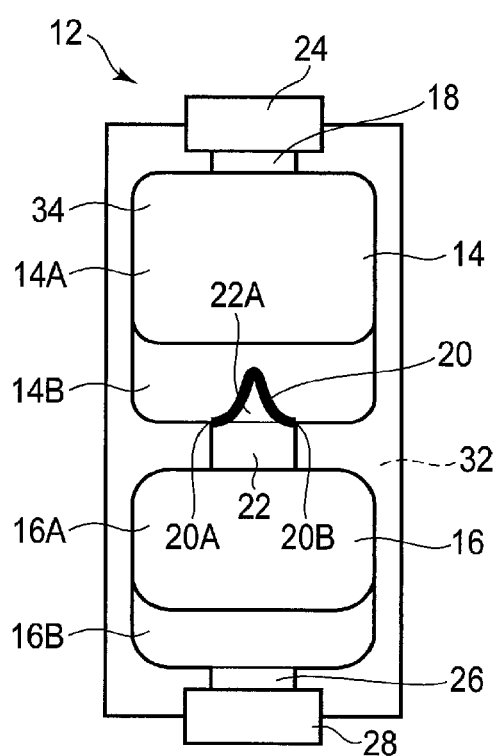
F I G. 10

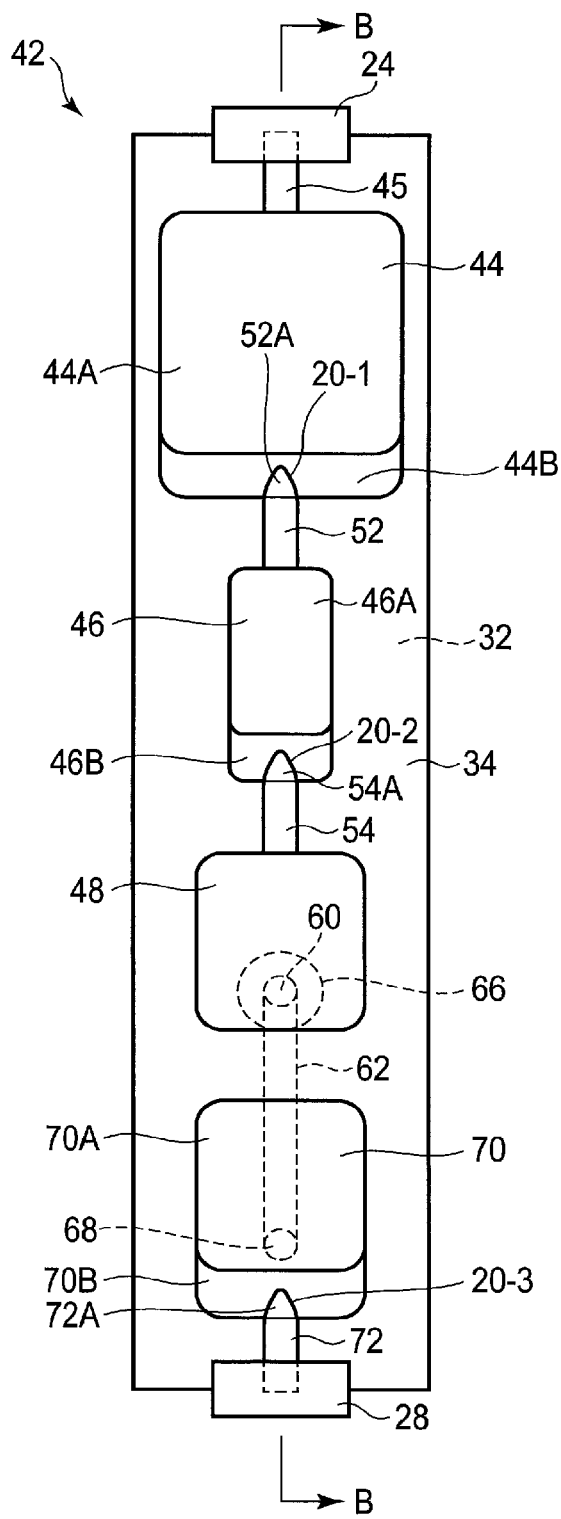
F I G. 11

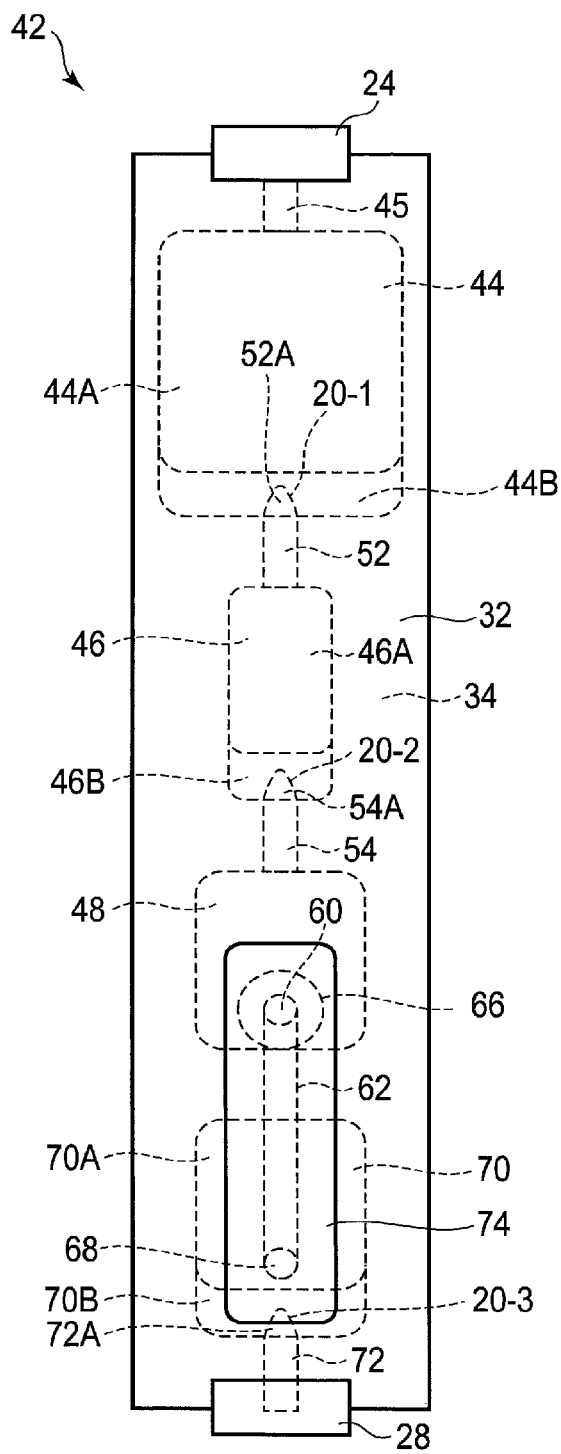
F I G. 13

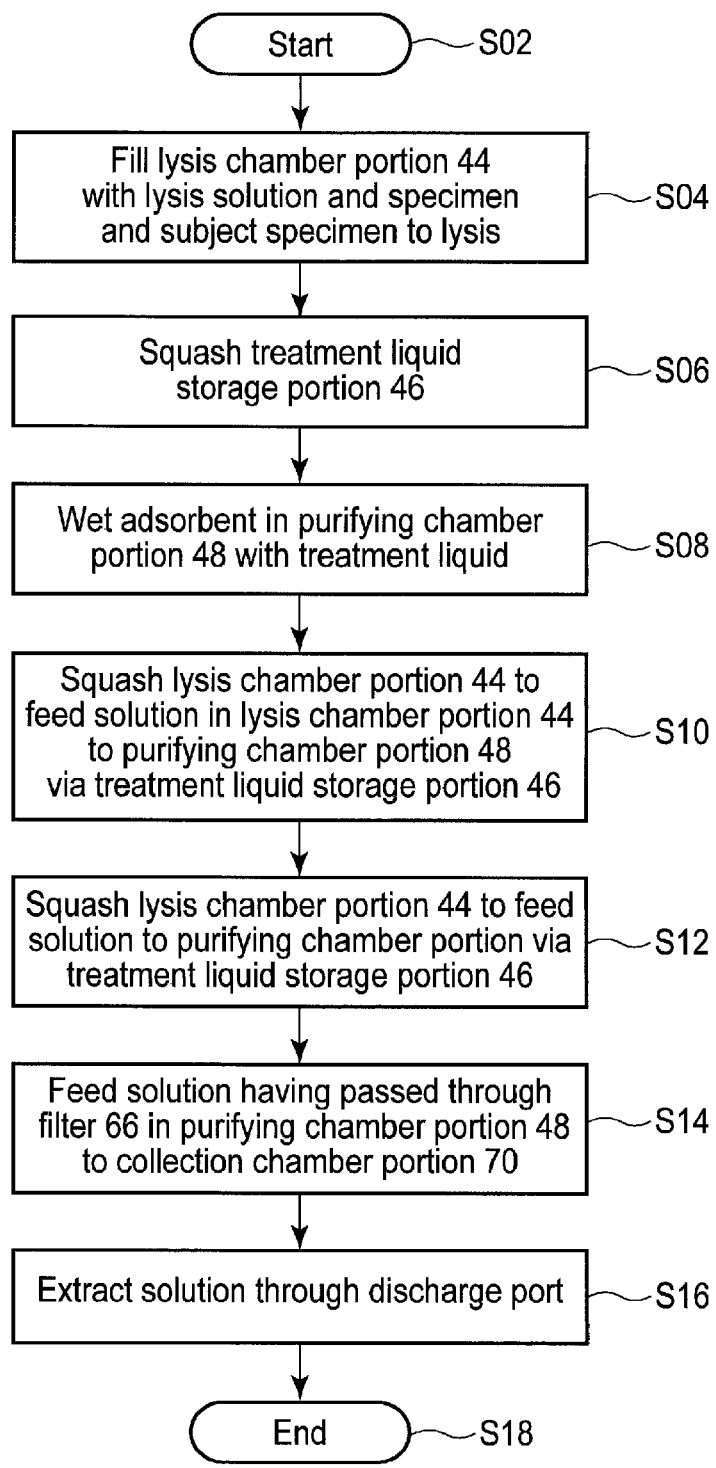
F I G. 14

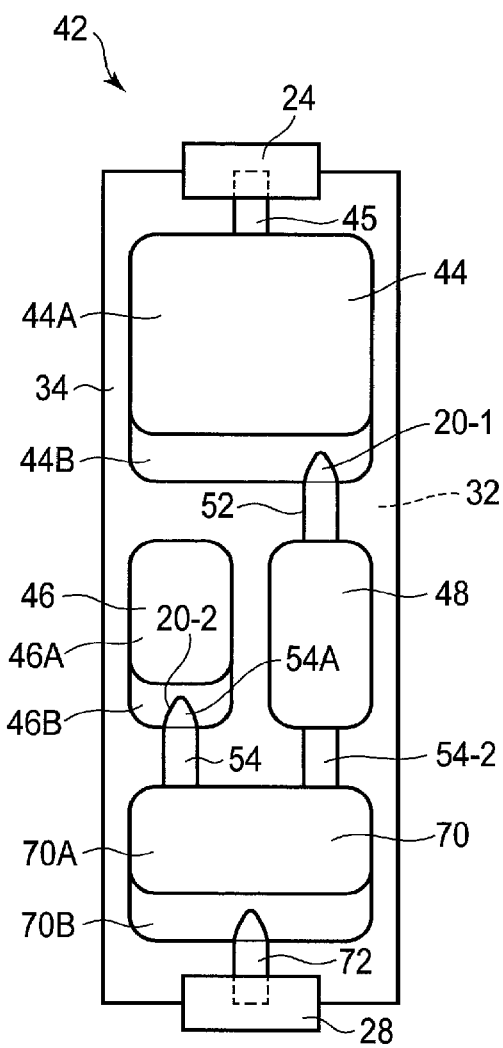
F I G. 19

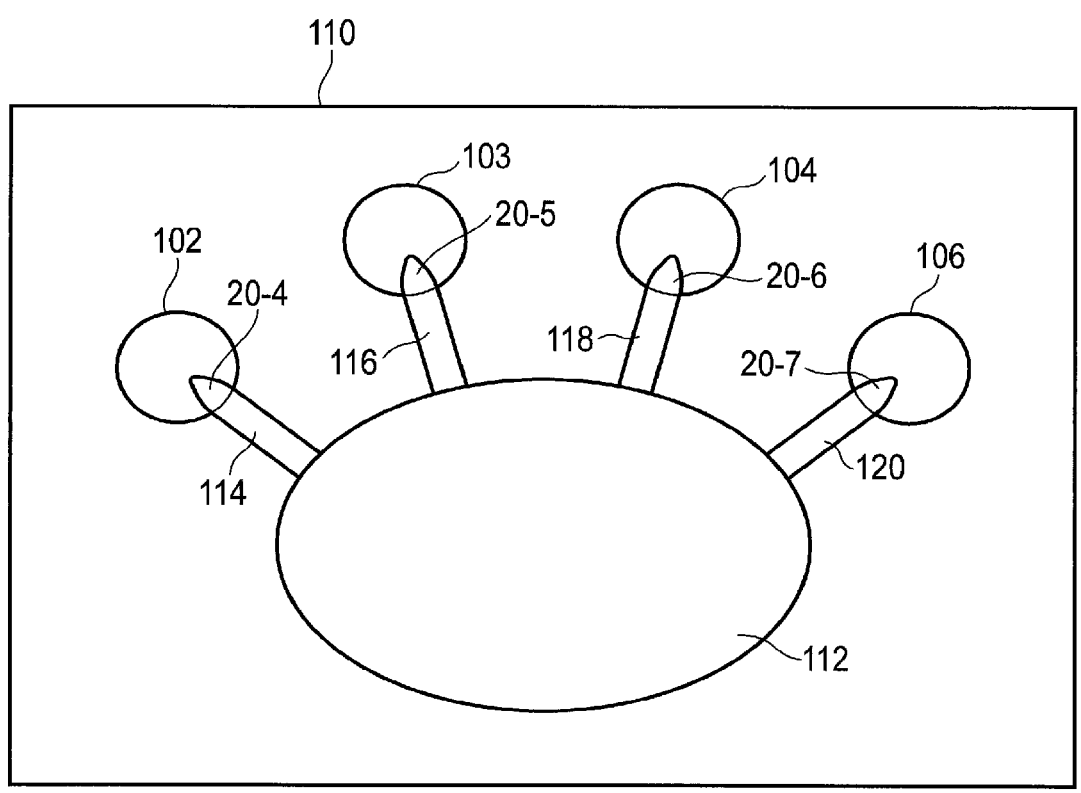
F I G. 20

| Type | Sheet thickness t [mm] | Equivalent stress [Mpa] | | Stress ratio |
| --- | --- | --- | --- | --- |
| | | Secondary seal | Max | |
| Comparative example | 0.15 | 0.53 | 13.4 | 4.00% |
| Embodiment 9 | 0.15 | 10.6 | 17.9 | 59.20% |
| Embodiment 10 | 0.15 | 14.7 | 24 | 61.30% |

F I G. 24

CHEMICAL CONTAINER

CROSS-REFERENCE TO RELATED APPLICATIONS

This application is based upon and claims the benefit of priority from Japanese Patent Application No. 2016-193602, filed Sep. 30, 2016, the entire contents of which are incorporated herein by reference.

FIELD

Embodiments described herein relate generally to a sealed chemical container comprising a peelable seal portion which isolates a compartment from a liquid feeding passage.

BACKGROUND

Various types of sealed chemical containers for respective intended purposes are available. For example, in some sealed chemical containers, a plurality of solutions or drugs is separately stored in compartments that are separated from one another with brittle heat seals. In such chemical containers, when the plurality of solutions or drugs is mixed together, the brittle heat seals are peeled off to bring the compartments into communication with one another to mix the solutions or drugs together, and the resultant solution is taken out as needed.

Some testing containers are used for testing in the form of sealed chemical containers. Such testing containers adopt a configuration in which an opening cap is threadably fitted over a container having closed compartments separated from one another by closing walls so that the opening cap is screwed to cut the closing walls to allow the content of the container to be discharged. Other chemical containers which enable more complicated treatments utilizing a plurality of compartments are also available.

Recently, there is demand for an improved sealed chemical container having a simple structure which permits a mixing of different contents with realizing a compact size and a low cost.

BRIEF DESCRIPTION OF THE DRAWINGS

FIG. 8 is a front view of a structure of a sealed chemical container according to a sixth embodiment.

FIG. 9 is a front view of a structure of a sealed chemical container according to a seventh embodiment.

FIG. 10 is a front view of a structure of a sealed chemical container according to an eighth embodiment.

FIG. 11 is a front view schematically depicting a pre-treatment kit according to an embodiment for extracting nucleic acid from a biological tissue, the pre-treatment kit having the structure of the above-described various sealed chemical containers.

FIG. 13 is a rear view schematically illustrating a rear surface of the pre-treatment kit depicted in FIG. 11.

FIG. 14 is a flowchart illustrating a treatment operation in a nucleic acid extraction apparatus in which the pre-treatment kit depicted in FIG. 11 is installed.

FIG. 19 is a front view schematically depicting a pre-treatment kit configured to extract nucleic acid from a biological tissue according to another embodiment and having the structure of the sealed chemical containers according to the above-described various embodiments.

FIG. 20 is a front view schematically depicting a biological and chemical treatment kit according to yet another embodiment having the structure of the sealed chemical containers according to the above-described various embodiments.

FIG. 24 is a table illustrating a comparison of peel-off characteristics between the sealed chemical container depicted in FIG. 21 and the sealed chemical container depicted in FIG. 22 and FIG. 23.

DETAILED DESCRIPTION

Various embodiments will be described hereinafter with reference to the accompanying drawings. In general, according to one embodiment, a chemical container comprises: a plate, a flexible sheet-like member including a bonding area fixedly bonded to the plate, the bonding area defining a first compartment enabled to be swollen on the plate and an outflow passage communicating with the first compartment via an opening thereof, and a first seal portion located in the first compartment and weakly bonded to the plate compared to the bonding area so as to close the opening with the sheet-like member, the first seal portion defining an area protruding from the opening toward the first compartment, and the first seal portion blocking communication between the first compartment and the outflow passage, wherein the first seal portion is peeled off by an increase in an internal pressure of the first compartment to swell the first compartment.

In embodiments, a sealed chemical container according to any of the embodiments is applied to a pre-treatment kit into which a lysis solution and then a biological tissue from an animal, a plant, microorganisms, or the like, or microorganisms, bacteria, fungi, or viruses (hereinafter simply referred to as a biological tissue) are fed and subjected to lysis and which allows nucleic acid to be extracted from the solution. In this case, instead of subjecting the biological tissue to lysis with a lysis solution, it is also preferable to inject a solution in which a biological tissue has been subjected to lysis into the sealed chemical container according to any of the embodiments. Alternatively, the biological tissue may be subjected to lysis in the sealed chemical container using physical means. The embodiments are applicable not only to sealed chemical containers with a lysis solution stored therein but also to a wide variety of sealed chemical containers such as testing containers for which liquid specimens or reagents are used or chemical containers in which solutions such as food solutions or fluid contents are sealed.

Sealed chemical containers according to various embodiments will be described below with reference to the drawings.

First Embodiment

Figure 1:
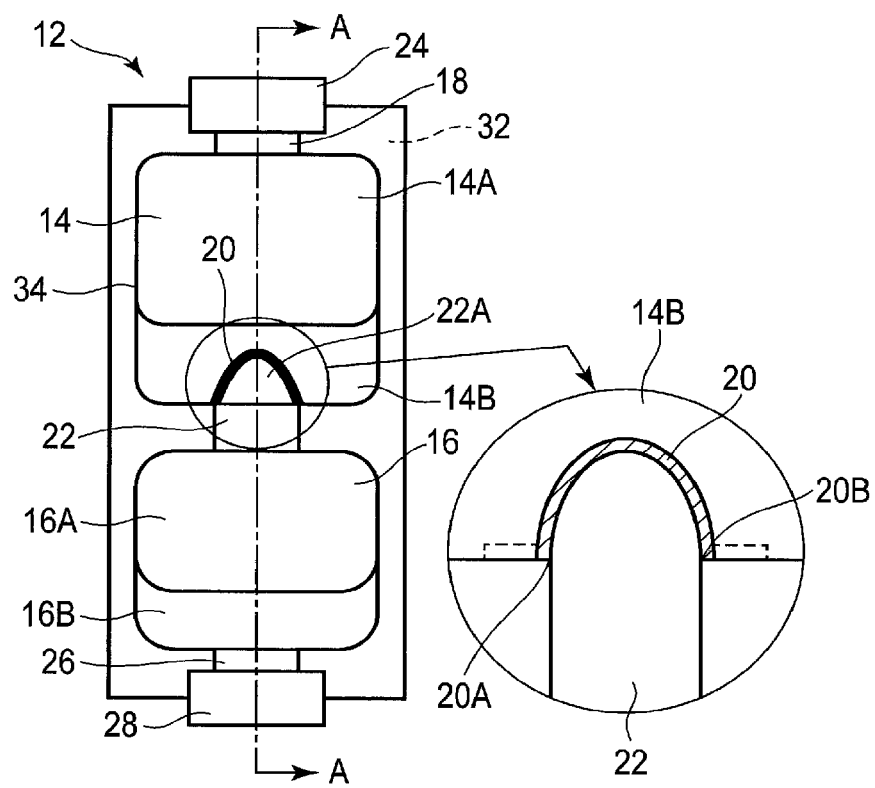
FIG. 1 is a front view schematically depicting a structure of a sealed chemical container according to a first embodiment.
Figure 2:
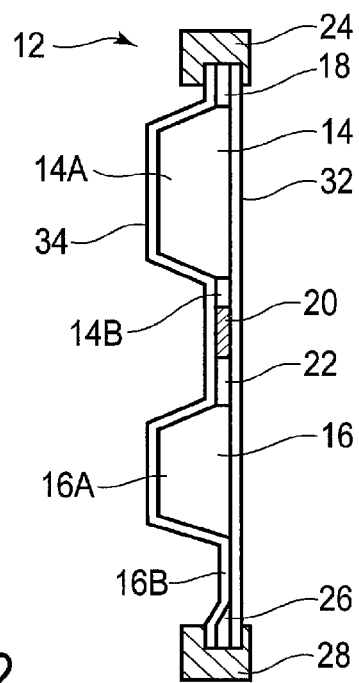
FIG. 2 is a cross-sectional view schematically illustrating a sectional structure of the sealed chemical container depicted in FIG. 1, the cross-sectional view being taken along line A-A in FIG. 1.

FIG. 1 and FIG. 2 schematically depict a configuration of a sealed chemical container 12 according to a first embodiment. The sealed chemical container 12 comprises a first compartment 14 on an upstream side and a second compartment 16 on a downstream side with respect to the first compartment 14 so that a content such as a test liquid or a solution is stored in each of the first compartment 14 and the second compartment 16. (The content is hereinafter simply referred to as a solution.) The sealed chemical container 12 is formed (primary seal) by fusing a flexible surface sheet 34 onto a rigid board-like plate (substrate) 32.

The first compartment 14 comprises a swollen portion 14A in which the surface sheet 34 is swollen into a substantially rounded rectangle and a deformed portion 14B in which, in the compartment, the surface sheet 34 is squashed and deformed into contact with the board-like plate 32. The swollen portion is formed by partitioning an area on the plate 32 at bonding areas where the surface sheet 34 is firmly sealed (primary seal) to the board-like plate 32. The primary seal, for example, allows the sheet and the plate to be thermally welded and integrated together. In the deformed portion 14B, a band-like or curved striped seal portion 20 is formed as a secondary seal portion (i.e., peelable portion), in which the surface sheet 34 sealed to the board-like plate 32 can be peeled off from the board-like plate 32 without being broken. In the seal portion (peelable portion) 20, the surface sheet 34 is obviously sufficiently weakly bonded to the board-like plate compared to the seal (primary seal). The band-like seal portion (peelable portion) 20 partitions the deformed portion 14B which can communicate with a second passage 22 located at the downstream-side of the first compartment 14, and serves as a blocking portion which blocks the communication passage to isolate (block) the first compartment 14 from the second passage 22. When the first compartment 14 is externally pressed, an internal pressure in the first compartment 14 is increased. The increase in pressure allows the deformed portion 14B to be swollen so as to be pushed open, peeling off the band-like seal portion (peelable portion) 20 from a bottom surface of the compartment 14. The swollen deformed portion 14B is brought into communication with the second passage 22. When the first compartment 14 is externally pressed, by way of example, the pressed portion is squashed to fold and deform the rounded cubic shape, which is thus pushed open and swollen.

In the first compartment 14, the swollen portion 14A is in communication with a first passage 18 located on the upstream side and which opens to the outside. The first passage 18 opens to the outside, with the opening (feeding port) thereof closed with a closing cap 24 in an openable manner. The first passage 18 is set to be narrower than the swollen portion 14A. When the closing cap 24 is removed from the opening, a solution is fed into the first compartment 14 via the opening (feeding port) from the outside of the chemical container 12, which is closed with the opening cap 24. Therefore, the first compartment 14 is sealed with the closing cap 24 and the band-like seal portion (peelable portion) 20 and is kept isolated from the outside.

The band-like seal portion 20 closes the opening side of the second passage 22 and provides an expanded portion 22A which is partitioned in the first compartment 14 which is in communication with the second passage 22. That is, the band-like seal portion 20 extends into the first compartment 14 in a peelable manner so as to isolate the expanded portion 22A in the first compartment 14. More specifically, base portions 20A, 20B at the respective ends of the band-like seal portion 20 substantially coincide with the opening of the second passage 22 to seal the opening of the second passage 22, defining the expanded portion 22A inside the band-like seal portion 20. As depicted in FIG. 1, the band-like seal portion 20 is formed like an inverted U shape having a tip portion protruding into the first compartment 14, and has one top portion gently curved so as to enable the band-like seal portion 20 to be easily peeled off. As described below n various embodiments, the top portion of the band-like seal portion 20 may be formed like a sharp portion in which a side of the band-like seal portion 20 located in the first compartment 14 is sharp or a rounded leading portion. An inner surface of the band-like seal portion 20 is preferably flush with an inner surface of the second passage 22. However, during a process of forming the band-like seal portion 20, a slight step may be formed between the inner surface of the band-like seal portion 20 and the inner surface of the second passage 22. The base portions 20A, 20B of the band-like seal portion 20 may be formed to extend along the inner surface of the first compartment 14 as depicted by a dashed line in the deformed portion 14B.

Like the first compartment 14, the second compartment 16 comprises a swollen portion 16A corresponding to a substantially rounded rectangle into which the surface sheet 34 is swollen and a deformed portion 16B in which the surface sheet 34 is squashed and deformed into contact with the board-like plate 32 in the compartment. The second passage 22 is in communication with the swollen portion 16A of the second compartment 16, and the deformed portion 16B of the second compartment 16 is in communication with a third passage 26 on the downstream side. Unlike the first compartment 14, the second compartment 16 is not provided with the seal portion (peelable portion) 20 corresponding to the secondary seal, and may thus be formed into the swollen portion 16A formed wholly of the primary seal or into the squashed deformed portion 16B. The third passage 26 has an opening (ventilation port) which opens to the outside, and allows the solution in the second compartment 16 to be discharged to the outside via the third passage 26 and the opening (ventilation port). For discharge of the solution, the swollen body swollen and rounded by inflow of the solution is pressed, and the pressed portion is squashed, allowing the solution to be discharged to the outside via the third passage 26 and the opening (ventilation port). The opening is closed with the closing cap 28 in an openable manner, enabling the inside of the second compartment 16 to be formed into a closed space and allowing prevention of a situation where an external environment is inadvertently contaminated.

As described above, the flexible surface sheet 34 is pre-embossed so as to form cavity areas corresponding to the first and second compartments 14, 16, the passages 18, 22, 26, and the opening, and is thus pre-provided with the swollen portions which appear at the time of swelling. Areas of the flexible surface sheet 34 other than the cavity areas are thermally welded and fixed or fixedly bonded to the board-like plate 32 so as to form a firm primary seal while being unable to be peeled off. After the surface sheet 34 is formed into the primary seal to the plate 32, all or a part of the swollen portions of the surface sheet 34 is squashed, and a squashed portion of the surface sheet 34 corresponding to the first compartment 14 is welded in a band form to form the band-like seal portion 20 serving as the secondary seal. An increasing pressure on the first compartment 14 gradually activates the secondary seal in a peelable manner. The secondary seal is set to be peeled off by a lower stress than the primary seal. The secondary seal is provided in the first compartment 14 and has a sufficient seal force to inhibit the seal from being easily peeled off by a fluid content.

Figure 3:
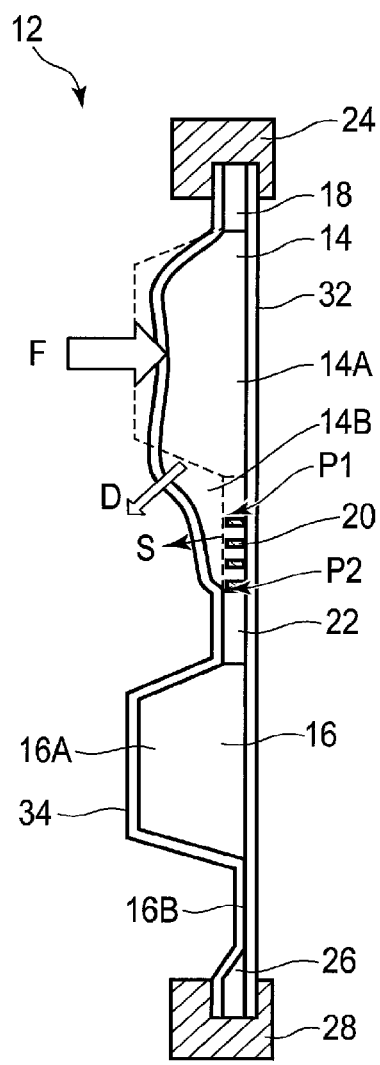
FIG. 3 is a schematic diagram schematically illustrating a peel-off process for a seal portion of the sealed chemical container depicted in FIG. 1.

In the above-described sealed chemical container 12, when the closing cap 24 is removed from the opening (input port) to feed the content such as a solution into the first compartment 14 and the opening is closed with the closing cap 24, the solution is sealed in the sealed chemical container 12. In this state, when a process needed for the internal solution (for example, a heating treatment, a crushing treatment, or a solution mixing treatment) is executed, the solution in the first compartment 14 is ready to be transferred to the second compartment 16. In this state, when a pressing force F is externally applied to the first compartment 14 as depicted in FIG. 3, the first compartment 14 depicted by a dashed line is deformed as depicted by a solid line to increase the pressure in the first compartment 14, and the squashed portion of the swollen portion forming the first compartment 14 gradually swells as depicted by arrow D. A stress P1 is applied so as to concentrate at the top portion of the band-like seal portion 20. Therefore, the top portion of the band-like seal portion 20 or a nearby part of the flexible surface sheet 34 peels off from the board-like plate, and the range of peel-off extends to peel off the band-like seal portion 20 from the board-like plate 32. As a result, the band-like seal portion 20 disappears, and the squashed deformed portion 14B of the first compartment 14 is fully expanded to bring the passage 22 into communication with the first compartment 14. Therefore, the solution in the first compartment 14 flows into the second compartment 16. If a content is present in the second compartment 16, the content mixes or reacts with the incoming solution to enable the solution to be discharged. Removal of the closing cap 28 allows a mixture solution or reaction solution is discharged to the outside via the third passage 26 and the opening (ventilation port).

In the sealed chemical container 12, the primary seal allows the surface sheet 34 and the plate 32 to be firmly thermally welded together so that the respective opposite surfaces of the surface sheet 34 and the plate 32 will not peel off except for the cavity portions, as described above. If the surface sheet 34 and the plate 32 are thermally welded together using the primary seal, the surface sheet 34 and the plate 32 are desirably formed of the same material. For example, the surface sheet 34 and the plate 32 are desirably formed of a thermoplastic resin, for example, polypropylene or polyethylene. If the surface sheet 34 and the plate 32 are integrated together using an adhesive or any other means instead of welding, the surface sheet 34 and the plate 32 may be formed of different materials.

The following description relates to the reason why, in the sealed chemical container 12 depicted in FIG. 1 to FIG. 3, the band-like seal portion 20 is relatively easily peeled off when a predetermined pressing force is applied to the first compartment 14, whereas the band-like seal portion 20 is not easily peeled off even when a stronger pressing force is applied to the second compartment 16.

During the process of peeling off the band-like seal portion 20, the stress 21 is applied so as to concentrate at the top portion of the band-like seal portion 20, which is thus pushed open and peeled off, as depicted in FIG. 3. In contrast, before the stress P1 is applied, external deformation pressure increases an internal pressure in the second compartment 16, and a stress P2 approximately equal to or higher than the stress 21 is applied to the band-like seal portion 20 from the passage 22 side. The stress 22 is dispersively and evenly applied to the curved portion of the band-like seal portion 20 located on the passage 22 side thereof without concentrating at the passage 22 side end of the band-like seal portion 20 corresponding to the top portion thereof partly because push-open deformation corresponding to the deformed portion 16B does not occur on the passage 22 side. Such application of the stress P2 is free from stress concentration which may cause peel-off of the band-like seal portion 20. Thus, the band-like seal portion 20 is more unlikely to peel off from the second compartment side faced to the second compartment 16 than from the first compartment side faced to the first compartment 14.

To inhibit generation of the stress P2, for example, during transportation of the sealed chemical container, the second compartment 16 is preferably kept in a state where a part of the surface sheet 34 forming the swollen portion remains squashed, to avoid inadvertent generation of the stress P2. Similarly, the first compartment 14 preferably has an outer periphery thereof protected with a relatively rigid cover or a relatively rigid outer case in a keeping and carrying conditions, so as to inhibit generation of the stress P1 resulting from inadvertent external pressing of the first compartment 14.

The sealed chemical container 12 depicted in FIG. 1 to FIG. 3 may have the structure of the sealed chemical container 12 with the seal portion 20 according to a second embodiment to an eighth embodiment depicted in FIG. 4 to FIG. 10. The structure of the sealed chemical container 12 according to the second embodiment to the eighth embodiment will be described with reference to FIG. 4 to FIG. 10. In the following description of the embodiments, components or portions denoted by the same reference numerals as those in FIG. 1 to FIG. 3 represent the same components or portions and will not be described for simplification.

Second Embodiment

Figure 4:
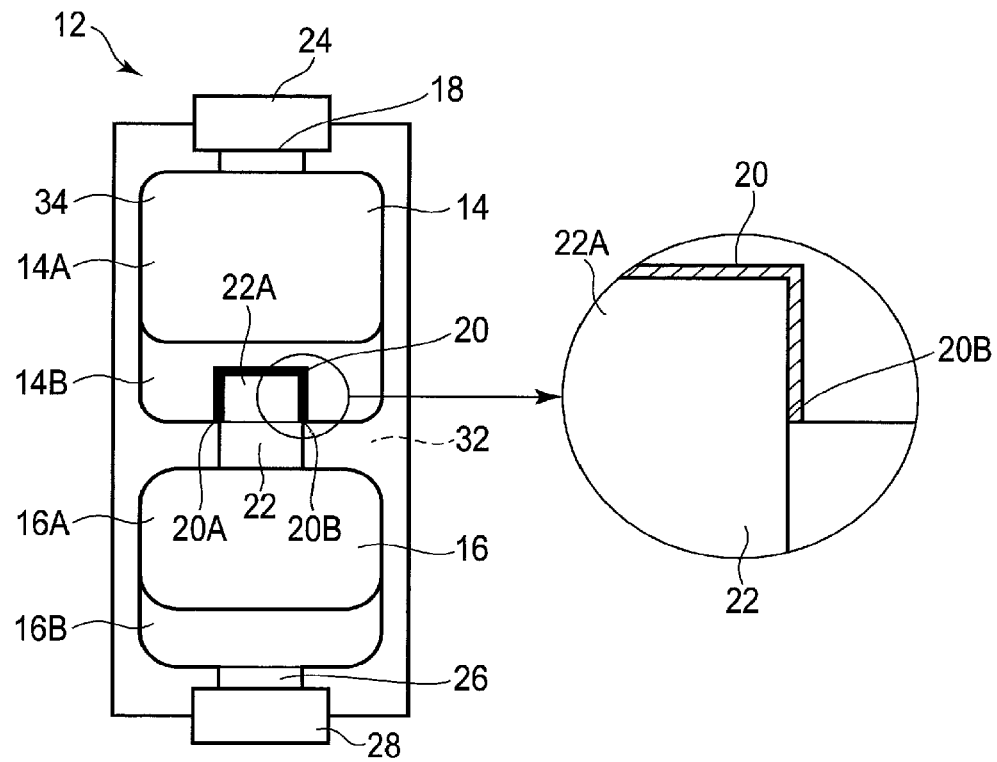
FIG. 4 is a front view of a structure of a sealed chemical container according to a second embodiment.

FIG. 4 depicts the sealed chemical container 12 according to the second embodiment. In the sealed chemical container 12, the band-like seal portion 20 is formed in the deformed portion 14B so as to have a rectangular box shape with two vertices (sharp portions). The band-like seal portion 20 extends into the first compartment 14 so as to provide, in the first compartment 14, a rectangular expanded portion 22A which is in communication with the second passage 22 and to isolate the expanded portion 22A in the first compartment 14, in a peelable manner. More specifically, the base portions 20A, 20B at the respective ends of the band-like seal portion 20 substantially coincide with the opening of the second passage 22, and the band-like seal portion 20 is formed substantially flush with the inner surface of the second passage 22.

As the pressure in the first compartment 14 increases, the rectangular box shaped band-like seal portion 20 is peeled off starting at the vertex sides, with the expanded portion 22A swollen. The first compartment 14 is brought into communication with the second passage 22. In this structure, even with an increase in the pressure in the second compartment 16, the pressure is substantially evenly dispersed inside the band-like seal portion 20 (inside the rectangular box shape) communicating with the second passage 22. The band-like seal portion 20 is thus inhibited from being easily peeled off in spite of the increase in the pressure of the first compartment 14.

Third Embodiment

Figure 5:
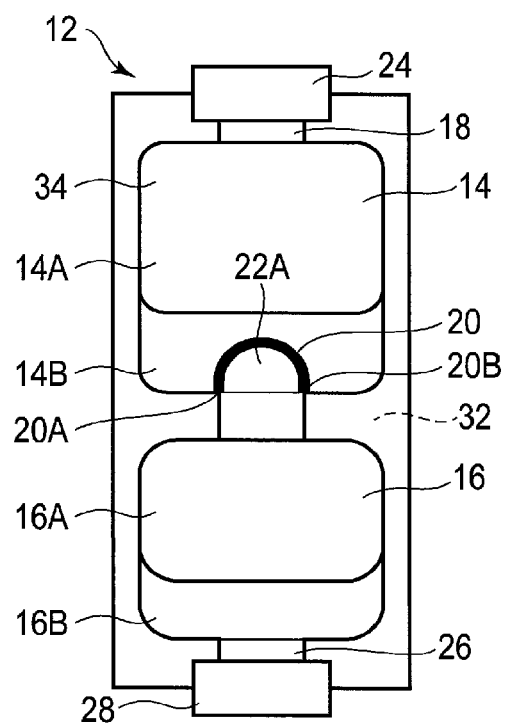
FIG. 5 is a front view of a structure of a sealed chemical container according to a third embodiment.

FIG. 5 denotes the sealed chemical container 12 according to the third embodiment. In the sealed chemical container 12, the band-like seal portion 20 is formed in the deformed portion 14B so as to have a leading portion with a semicircular shape. The band-like seal portion 20 extends into the first compartment 14 so as to provide, in the first compartment 14, a semicircular expanded portion 22A which is in communication with the second passage 22 and to isolate the expanded portion 22A in the first compartment 14, in a peelable manner.

As the pressure in the first compartment 14 increases, the semicircular band-like seal portion 20 is peeled off starting at a vertex side of the semicircle, with the expanded portion 22A swollen. The first compartment 14 is brought into communication with the second passage 22. In this structure, even with an increase in the pressure in the second compartment 16, the pressure is substantially evenly dispersed inside the band-like seal portion 20 (inside the semicircle) communicating with the second passage 22. The band-like seal portion 20 is thus inhibited from being easily peeled off in spite of the increase in the pressure of the first compartment 14.

Fourth Embodiment

Figure 6:
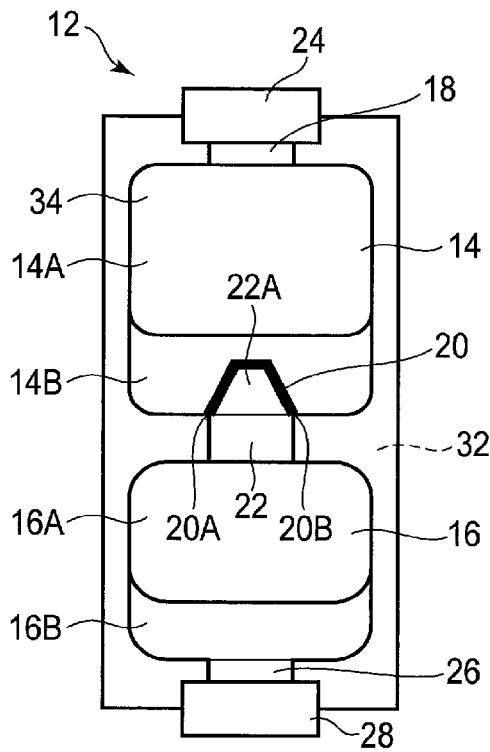
FIG. 6 is a front view of a structure of a sealed chemical container according to a fourth embodiment.

FIG. 6 denotes the sealed chemical container 12 according to the fourth embodiment. In the sealed chemical container 12, the band-like seal portion 20 is formed in the deformed portion 14B so as to have a trapezoidal shape with two vertices (sharp portions). The band-like seal portion 20 extends into the first compartment 14 so as to provide, in the first compartment 14, a trapezoidal expanded portion 22A which is in communication with the second passage 22 and to isolate the expanded portion 22A in the first compartment 14 in a peelable manner.

As the pressure in the first compartment 14 increases, the trapezoidal band-like seal portion 20 is peeled off starting at two vertex sides of the trapezoid, with the expanded portion 22A swollen. The first compartment 14 is brought into communication with the second passage 22. In this structure, even with an increase in the pressure in the second compartment 16, the pressure is substantially evenly dispersed inside the band-like seal portion 20 (inside the trapezoid) communicating with the second passage 22. The band-like seal portion 20 is thus inhibited from being easily peeled off in spite of the increase in the pressure of the first compartment 14.

Fifth Embodiment

Figure 7:
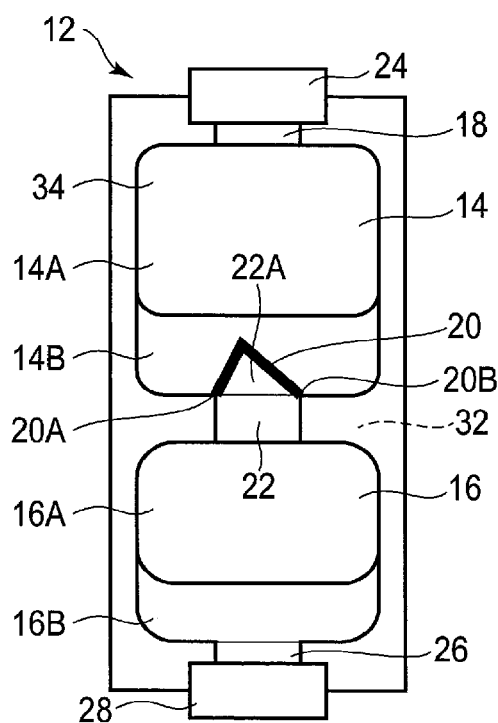
FIG. 7 is a front view of a structure of a sealed chemical container according to a fifth embodiment.

FIG. 7 denotes the sealed chemical container 12 according to the fifth embodiment. In the sealed chemical container 12, the band-like seal portion 20 is formed in the deformed portion 14B so as to have a scalene triangle shape with one vertex (sharp portion). The band-like seal portion 20 extends into the first compartment 14 so as to provide, in the first compartment 14, a scalene triangle-shaped expanded portion 22A which is in communication with the second passage 22 and to isolate the expanded portion 22A in the first compartment 14, in a peelable manner.

As the pressure in the first compartment 14 increases, the triangular band-like seal portion 20 is peeled off starting at the one vertex side of the triangle, with the expanded portion 22A swollen. The first compartment 14 is brought into communication with the second passage 22. In this structure, even with an increase in the pressure in the second compartment 16, the pressure is substantially evenly dispersed inside the band-like seal portion 20 (inside the triangle) communicating with the second passage 22. The band-like seal portion 20 is thus inhibited from being easily peeled off in spite of the increase in the pressure of the first compartment 14.

Sixth Embodiment

FIG. 8 denotes the sealed chemical container 12 according to the sixth embodiment. In the sealed chemical container 12, the band-like seal portion 20 is formed in the deformed portion 14B so as to have an inversed W shape with two vertices. The band-like seal portion 20 extends into the first compartment 14 so as to provide, in the first compartment 14, a trapezoidal expanded portion 22A which is in communication with the second passage 22 and to isolate the expanded portion 22A in the first compartment 14 in a peelable manner.

As the pressure in the first compartment 14 increases, the inversed-W-shaped band-like seal portion 20 is peeled off starting at the two vertex sides of the inversed W shape, with the expanded portion 22A swollen. The first compartment 14 is brought into communication with the second passage 22. In this structure, even with an increase in the pressure in the second compartment 16, the pressure is substantially evenly dispersed inside the band-like seal portion 20 (inside the inversed W shape) communicating with the second passage 22. The band-like seal portion 20 is thus inhibited from being easily peeled off in spite of the increase in the pressure of the first compartment 14.

Seventh Embodiment

FIG. 9 denotes the sealed chemical container 12 according to the seventh embodiment. In the sealed chemical container 12, the band-like seal portion 20 is formed in the deformed portion 14B so as to have an isosceles triangle shape with one vertex (sharp portion). The band-like seal portion 20 extends into the first compartment 14 in a peelable manner so as to provide, in the first compartment 14, an isosceles triangle-shaped expanded portion 22A which is in communication with the second passage 22 and to isolate the expanded portion 22A in the first compartment 14.

As the pressure in the first compartment 14 increases, the triangular band-like seal portion 20 is peeled off starting at the one vertex side of the triangle, with the expanded portion 22A swollen. The first compartment 14 is brought into communication with the second passage 22. In this structure, even with an increase in the pressure in the second compartment 16, the pressure is substantially evenly dispersed inside the band-like seal portion 20 (inside the triangle) communicating with the second passage 22. The band-like seal portion 20 is thus inhibited from being easily peeled off in spite of the increase in the pressure of the first compartment 14.

Eighth Embodiment

FIG. 10 denotes the sealed chemical container 12 according to the eighth embodiment. In the sealed chemical container 12, the band-like seal portion 20 is formed in the deformed portion 14B so as to have a chevron shape with one vertex (sharp portion). The band-like seal portion 20 extends into the first compartment 14 in a peelable manner so as to provide, in the first compartment 14, a chevron-shaped expanded portion 22A which is in communication with the second passage 22 and to isolate the expanded portion 22A in the first compartment 14.

As the pressure in the first compartment 14 increases, the chevron-shaped seal portion 20 is peeled off starting at the one vertex side of the chevron, with the expanded portion 22A swollen. The first compartment 14 is brought into communication with the second passage 22. In this structure, even with an increase in the pressure in the second compartment 16, the pressure is substantially evenly dispersed inside the band-like seal portion 20 (inside the chevron) communicating with the second passage 22. The band-like seal portion 20 is thus inhibited from being easily peeled off in spite of the increase in the pressure of the first compartment 14.

The sealed chemical containers 12 depicted in FIG. 1 to FIG. 10 can be applied to various intended purposes, particularly to a pre-treatment kit allowing nucleic acid to be extracted from a biological tissue and for which prevention of scattering of the content of the container into an external environment is focused on. An embodiment of a pre-treatment kit for which the structure of the sealed chemical container 12 is adopted will be described below. Also in the following description of embodiments, components or portions denoted by the same reference numerals as those in FIG. 1 to FIG. 10 represent the same components or portions and will not be described for simplification.

Embodiments of the Pre-treatment Kit

Figure 12:
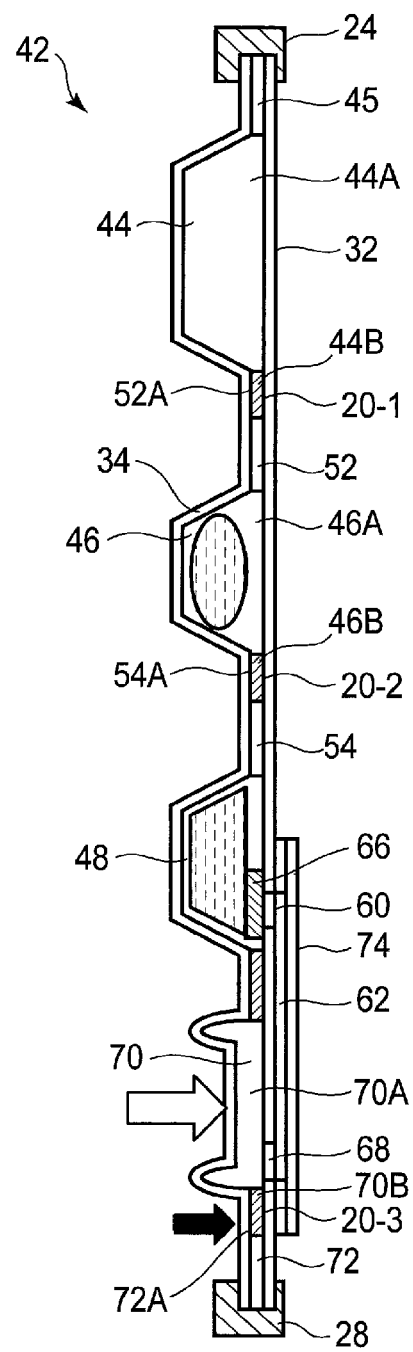
FIG. 12 is a side sectional view schematically illustrating a structure of the pre-treatment kit depicted in FIG. 11, the side sectional view being taken along line B-B in FIG. 11.
Figure 15:
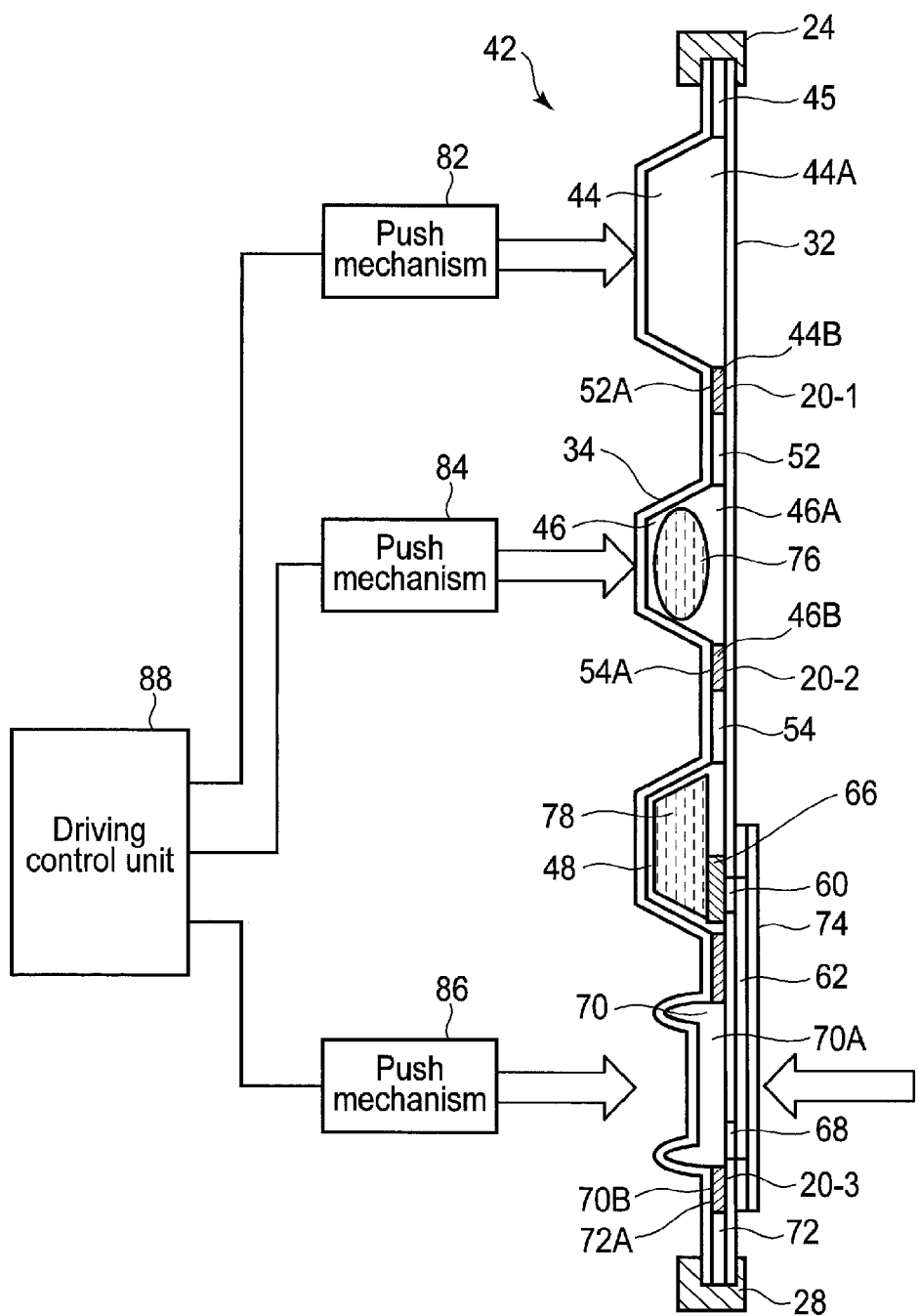
FIG. 15 is block diagram schematically depicting blocks of the nucleic acid extraction apparatus which extracts nucleic acid and in which the pre-treatment kit depicted in FIG. 11 is installed.

FIG. 11, FIG. 12, and FIG. 13 depict, as a ninth embodiment, a pre-treatment kit configured to extract nucleic acid from a biological tissue to purify the nucleic acid.

The pre-treatment kit 42 comprises a specimen passage portion 45, a lysis chamber portion 44, a solution passage 52, a treatment liquid storage portion 46, a treatment liquid passage 54, a purifying chamber portion 48, a channel groove 62, a collection chamber portion 70, and a collection passage 72. In the pre-treatment kit 42, the flexible surface sheet 34 is fused (thermally welded) onto the rigid board-like plate 32 to form a firm airtight pressure-sensitive seal, as is the case with the above-described sealed chemical container 12. Like the first compartment 14 and the second compartment 16, the lysis chamber portion 44, the treatment liquid storage portion 46, the purifying chamber portion 48, and the collection chamber portion 70 are shaped by embossing the flexible surface sheet 34 so that substantially rounded rectangular swollen portions can be formed when the surface sheet 34 is swollen. Likewise, the specimen passage portion 45, the solution passage 52, the treatment liquid passage 54, and the collection passage 72 are shaped like tubes by embossing the surface sheet 34 so that solutions can flow through the passages. The channel groove 62 is formed in a rear surface side of the board-like plate 32 and covered with a rear surface sheet 74 as depicted in FIG. 12 and FIG. 13. The rear surface sheet 74 is thermally welded to the rear surface of the board-like plate 32 so as to form a first pressure-adhesive seal to prevent solutions from flowing out from the channel groove 62.

The board-like plate 32 is formed of polypropylene or a similar resin material as described above. The surface sheet 34 is formed of a transparent resin film and made flexible enough to allow the swollen portions to be squashed with push rods (not depicted in the drawings) as is the case with the first and second compartments 14, 16. If the surface sheet 34 is sealed to the plate 32 by welding, the surface sheet 34 is formed of the same material as that of the plate 32, for example, a thermoplastic resin such as polypropylene or polyethylene. When integrated together using an adhesive or any other means instead of welding, the surface sheet 34 and the plate 32 may be formed of different materials.

The lysis chamber portion 44 is coupled to a tubular communication passage portion 45 to allow a solution containing a surfactant or the like to subject biological tissues to lysis to be fed through the opening of the communication passage portion 45 for housing. The opening of the communication passage portion 45 is closed with the cap portion 24. When nucleic acid is extracted, the cap portion 24 is removed and a biological tissue is fed into the lysis chamber portion 44 and subjected to lysis by the solution, with nucleic acid (DNA) in the biological tissue eluted into the solution. Instead of a lysis solution, a solution such as a simple reagent may be housed in the lysis chamber portion 44. For the pre-treatment kit 42 in which a solution such as a reagent is housed, the biological tissue may be crushed outside the pre-treatment kit 42, and the crushed biological tissue may be fed into the lysis chamber portion 44 to mix with the solution. After fed into the lysis chamber portion 44, the biological tissue may be crushed with beads externally vibrated by ultrasonic waves so that nucleic acid is eluted from the crushed biological tissue into the solution in the lysis chamber portion 44.

Like the first and second compartments 14, 16, the lysis chamber portion 44 comprises a swollen portion 44A and a deformed portion 44B formed by collapsing the surface sheet 34 so as to bring the surface sheet 34 into contact with the board-like plate 32 in the compartment. The deformed portion 44B is provided with a band-like seal portion, i.e., a peelable curved stripe portion 20-1 which allows the surface sheet 34 to be peeled off from the board-like plate 32 without breaking the surface sheet 34. The band-like seal portion (peelable portion) 20-1 extends in a peelable manner into the lysis chamber portion 44 so as to provide an expanded portion 52A which is in communication with the downstream-side solution passage 52 and to isolate the expanded portion 52A in the lysis chamber portion 44. Therefore, the downstream-side solution passage 52 is isolated from the solution passage 52 by the seal portion (peelable portion) 20-1. The band-like seal portion (peelable portion) 20 corresponds to the band-like seal portion (peelable portion) 20 described with reference to FIG. 1 to FIG. 10 and may take various forms.

When the lysis chamber portion 44 is externally pressed, the pressure in the lysis chamber portion 44 is increased. The increase in pressure allows the deformed portion 44B to be swollen to peel off the band-like seal portion (peelable portion) 20-1 from a bottom surface of the lysis chamber portion 44. The swollen deformed portion 44B is brought into communication with the solution passage 52. When the lysis chamber portion 44 is externally pressed, the pressed portion is squashed, folded, and deformed into a swollen body.

A treatment liquid (buffer solution) for wetting an adsorbent is stored in the treatment liquid storage portion 46. The purifying chamber portion 48 accommodates a reaction inhibitor which inhibits reaction during subsequent treatment steps or an adsorbent 78 which adsorbs contaminants and the like as impurities. The adsorbent 78 is, for example, a composite absorbent disclosed in Japanese Patent No. 5173406. A treatment liquid (buffer solution) with which the composite absorber is wetted and provided with a stable adsorption effect is, for example, a Tris-HCL buffer. However, the adsorbent 78 and the treatment liquid 76 are not limited to the above-described adsorbent and treatment liquid. Obviously, any adsorbent and any treatment liquid may be used so long as the adsorbent exerts an adsorption effect when wetted with the treatment liquid and the treatment liquid allows the adsorbent to be wetted.

The treatment liquid storage portion 46 and the purifying chamber portion 48 are also formed as, for example, deformable swollen portions formed by swelling the material so that the resultant portions appear like rounded rectangular parallelepipeds. Like the lysis chamber portion 44, the treatment liquid storage portion 46 comprises a swollen portion 46A and a deformed portion 46B formed by collapsing the surface sheet 34 so as to bring the surface sheet 34 into contact with the board-like plate 32 in the compartment. The deformed portion 46B is provided with a band-like seal portion (peelable portion) 20-2 which allows the surface sheet 34 to be peeled off from the board-like plate 32 without breaking the surface sheet 34. The band-like seal portion (peelable portion) 20-2 defines the treatment liquid storage portion 46 which can communicate with the downstream-side purifying chamber portion 48, and isolates the treatment liquid storage portion 46 from the treatment liquid passage 54. Like the band-like seal portion (peelable portion) 20-1, the band-like seal portion (peelable portion) 20-2 corresponds to the band-like seal portion (peelable portion) 20 described with reference to FIG. 1 to FIG. 10 and may take various forms.

The band-like seal portion 20-2 extends in a peelable manner into the treatment liquid storage portion 46 so as to provide, in the treatment liquid storage portion 46, an expanded portion 54A which is in communication with the treatment liquid passage 54 and to isolate the expanded portion 54A in the treatment liquid storage portion 46. As described with reference to FIG. 3, as the pressure in the treatment liquid storage portion 46 increases, the band-like seal portion 20-2 is peeled off starting at a vertex side thereof, with the expanded portion 54A swollen. The treatment liquid storage portion 46 is brought into communication with the treatment liquid passage 54. Even with an increase in the pressure in the treatment liquid storage portion 46, the pressure is substantially evenly dispersed inside the band-like seal portion 20-1 communicating with the treatment liquid passage 54. Therefore, the band-like seal portion 20-1 is inhibited from being easily peeled off in spite of the increase in the pressure of the treatment liquid storage portion 46.

A through-hole 60 is formed in a part of the board-like plate 32 which faces the purifying chamber portion 48, and communicates with the channel groove 62 formed in the rear surface of the board-like plate 32. A filter film 66 formed of PVDF is provided on the through-hole 60 in the purifying chamber portion 48. A purified solution containing nucleic acid to be tested which has failed to be adsorbed by the adsorbent in the purifying chamber portion 48 flows through the channel groove 62 via the filter film 66. The filter film 66 inhibits passage of pieces of an adsorbing material, and impurities and dust which have failed to be adsorbed (hereinafter simply referred to as contaminants and the like) to allow a solution which is free from contaminants and the like and which contains nucleic acid to flow into the channel groove 62 covered with the transparent rear surface sheet 74. An outflow end of the channel groove 62 is in communication with a through-hole 68 drilled in the board-like plate 32. The through-hole 68 opens into the collection chamber portion 70. The purified solution which is free from contaminants and the like and which contains nucleic acid flows into the collection chamber portion 70, where the solution is collected and stored as a specimen solution. To assist smooth inflow of the purified solution, the collection chamber portion 70 is kept in a state where the swollen portion is pre-squashed so that the collection chamber portion 70 is swollen by inflow of the purified solution. Preferably, even though not completely squashed, the swollen portion of the collection chamber portion 70 has a margin enough to inhibit airtightness of the collection chamber portion 70 from being impaired when the purified solution flows into the collection chamber portion 70 or when the collection chamber portion 70 is pushed.

The collection chamber portion 70 is in communication with the collection passage 72, and an opening of the collection passage 72 is covered with the closing cap 28 to close the collection passage 72. Like the board-like plate 32, the closing cap 28 is formed as a separate component using a resin such as polypropylene.

Like the lysis chamber portion 44, the collection chamber portion 70 comprises a swollen portion 70A and a deformed portion 70B formed by collapsing the surface sheet 34 so as to bring the surface sheet 34 into contact with the board-like plate 32 in the compartment. The deformed portion 70B is provided with a band-like seal portion (peelable portion) 20-3 which allows the surface sheet 34 to be peeled off from the board-like plate 32 without breaking the surface sheet 34. The band-like seal portion (peelable portion) 20-3 isolate, in the deformed portion 70B, an expanded portion 72A which can communicate with the downstream-side collection passage 72, and partitions the collection chamber portion 70 from the collection passage 72. Like the band-like seal portion (peelable portion) 20-1, the band-like seal portion (peelable portion) 20-3 corresponds to the band-like seal portion (peelable portion) 20 described with reference to FIG. 1 to FIG. 10 and may take various forms.

When the above-described nucleic acid pre-treatment kit 42 is manufactured, the granular adsorbent 78 is placed in the space in the purifying chamber portion 48 on the filter film 66, and the surface sheet 34 and the board-like plate 32 are strongly pressure-bonded together so that the adsorbent 78 is accommodated in the purifying chamber portion 48. During a process of manufacturing the pre-treatment kit 42, a treatment liquid (buffer solution) is injected and stored in the treatment liquid storage portion 46. For the injection and storage, by way of example, a through-hole (not depicted in the drawings) is formed in the board-like plate 32 so that the treatment liquid is fed into the treatment liquid storage portion 46 via the through-hole for housing. After the treatment liquid is fed into the treatment liquid storage portion 46 for housing, the through-hole is sealed. During storage or transportation of the pre-treatment kit 42, the treatment liquid storage portion 46 is preferably covered with a rigid protect cover (not depicted in the drawings) so as to inhibit the treatment liquid (buffer solution) from leaking from the treatment liquid storage portion 46 into the purifying chamber portion 48 when the swollen portion forming the treatment liquid storage portion 46 is pressed. While the pre-treatment kit 42 is not in use, the lysis chamber portion 44 and the collection chamber portion 70 are squashed so as to be swollen by inflow of a solution and can thus receive a liquid from the outside.

The above-described pre-treatment kit 42 is utilized for a nucleic acid extraction treatment in accordance with a procedure illustrated in FIG. 14. To allow nucleic acid to be extracted, the cap portion 24 is removed to expose the opening in the lysis chamber portion 44. The protect cover (not depicted in the drawings) which protects the treatment liquid storage portion 46 from being inadvertently pressed is removed. Thus, the treatment liquid storage portion 46 is exposed to the outside and can thus be pressed. The pre-treatment kit 42 is installed in an extraction apparatus comprising push mechanisms 82, 84, 86, and a nucleic acid extraction treatment is started (S02). The push mechanisms 82, 84, 86 comprise rods (none of which is illustrated) used to push the lysis chamber portion 44, the treatment liquid storage portion 46, and the collection chamber portion 70. A driving control unit 88 controllably drives the push mechanisms 82, 84, 86 to allow the corresponding rods to push the lysis chamber portion 44, the treatment liquid storage portion 46, and the collection chamber portion 70.

A lysis solution is injected into the treatment liquid storage portion 46 through the opening thereof. Subsequently, a biological tissue is injected into the lysis chamber portion 44 as a specimen (S04). Subsequently, the cap portion 24 is attached to the opening of the lysis chamber portion 44 to close the lysis chamber portion 44. As a result, in the closed lysis chamber portion 44, the biological tissue is subjected to lysis by the solution to elute nucleic acid (DNA) into the solution. In the biological tissue lysis step (S04), a solution containing the nucleic acid (DNA) to be tested and contaminants is prepared in the lysis chamber portion 44. In the lysis step (S04), a treatment may be executed in which the lysis chamber portion 44 is heated to heat the biological tissue to allow easy lysis of the biological tissue. The heating treatment is preferably ended before a shift to the next step.

Figure 16:
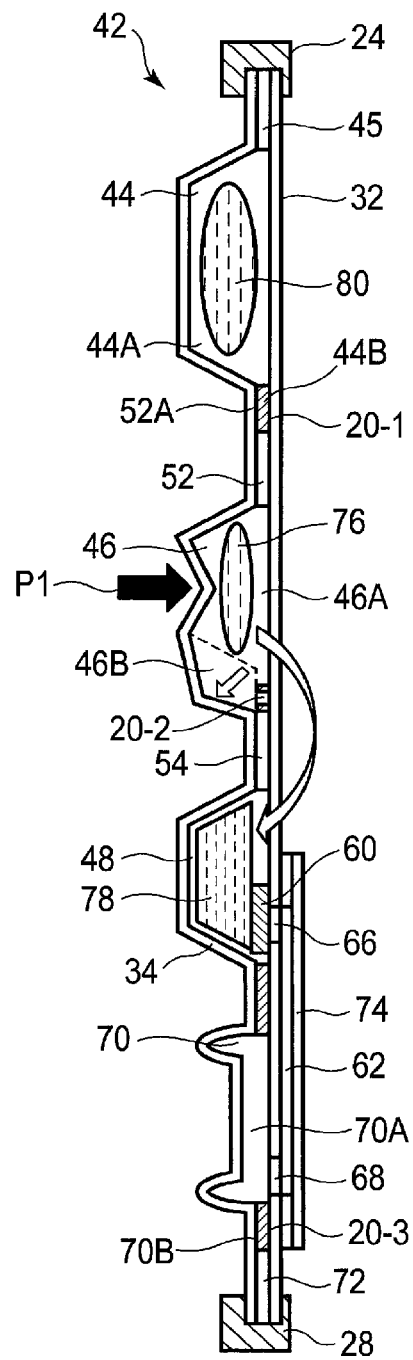
FIG. 16 is a side sectional view illustrating a treatment operation in the nucleic acid extraction apparatus in which the pre-treatment kit depicted in FIG. 11 is installed.

During lysis of the biological tissue, as depicted in FIG. 16, the push mechanism 82 is activated to allow the rod (not depicted in the drawings) driven by a motor to push the treatment liquid storage portion 46 as depicted by arrow P1, and the treatment liquid storage portion 46 is squashed (S06). As a result, the pressure in the treatment liquid storage portion 46 increases to peel off the seal portion (peelable portion) 20-2. The treatment liquid is then fed to the purifying chamber portion 48 via the treatment liquid passage 54 to wet the adsorbent 78 with the treatment liquid 76 (S08). When the treatment liquid storage portion 46 is externally pushed by a rod of an external apparatus or the like, the solution passage 52 remains closed by the seal portion (peelable portion) 20-1, and the seal of the seal portion (peelable portion) 20-2 is released by the pressure of the treatment liquid in the treatment liquid storage portion 46, allowing the treatment liquid to be fed to the purifying chamber portion 48. Feeding of the treatment liquid allows the granular adsorbent 78 to be wetted with the treatment liquid, activating the adsorption effect of the adsorbent.

Figure 17:
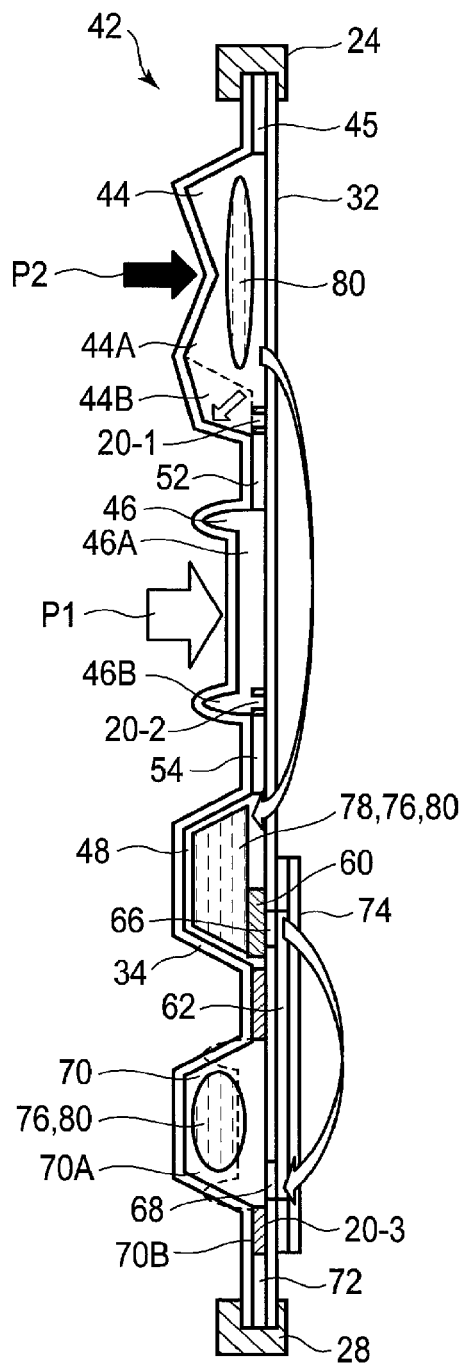
FIG. 17 is a side sectional view illustrating a treatment operation in the nucleic acid extraction apparatus in which the pre-treatment kit depicted in FIG. 14 is installed.

When the adsorbent activation treatment is completed, a separation step of separating the nucleic acid to be tested and the contaminants from the solution is executed. In the separation step, the push mechanism 82 is activated to allow the external rod (not depicted in the drawings) to squash the lysis chamber portion 44 as depicted by arrow P2 in FIG. 17. Therefore, the pressure in the lysis chamber portion 44 increases to allow the seal portion 20-1 to be peeled off by the solution of the lysis chamber portion 44, opening the solution passage 52, and the solution flows into the treatment liquid storage portion 46 via the solution passage 52 (S10). With the solution flowing into the treatment liquid storage portion 46, the swollen portion forming the treatment liquid storage portion 46 is swollen, but the treatment liquid storage portion 46 is squashed again by the external rod. Therefore, the solution flows through the treatment liquid storage portion 46 into the treatment liquid passage 54, and is then fed to the purifying chamber portion 48 via the treatment liquid passage 54 (S12). In this case, during the adsorbent activation treatment, the treatment liquid storage portion 46 may be squashed by the push rod, which may then be maintained in this position to keep the treatment liquid storage portion 46 squashed, and the solution in which the nucleic acid and the contaminants and the like have been subjected to lysis may be fed from the lysis chamber portion 44 to the purifying chamber portion 48 via the solution passage 52, the treatment liquid storage portion 46, and the treatment liquid passage 54.

In the purifying chamber portion 48, the contaminants contained in the solution as impurities are adsorbed by the adsorbent 78. In this purifying step, when the swollen portions forming the lysis chamber portion 44 and the treatment liquid storage portion 46 are squashed, the solution is directed toward the channel groove 62 through the filter 66 and the through-hole 60 in the purifying chamber portion 48. The filter film 66 inhibits passage of the contaminants and the like which have failed to be adsorbed by the adsorbent 78, and the solution which is free from the contaminants and the like and which contains the nucleic acid to be tested flows into the channel groove 62 via the filter film 66. The solution having flowed into the channel groove 62 flows into the collection chamber portion 70 and is then collected in the collection chamber portion 70.

Figure 18:
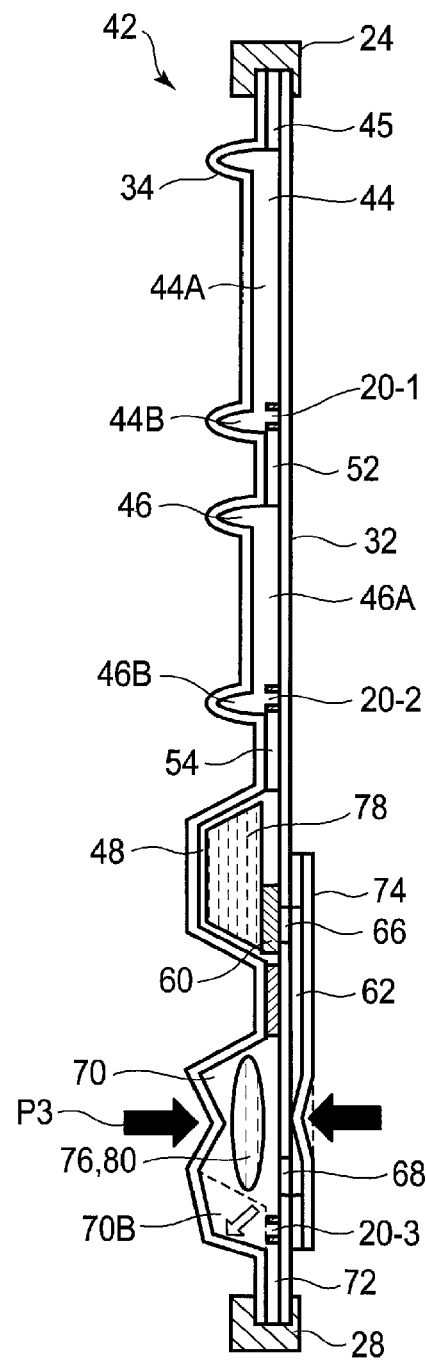
FIG. 18 is a side sectional view illustrating a treatment operation in the nucleic acid extraction apparatus in which the pre-treatment kit depicted in FIG. 14 is installed.

When a predetermined amount of solution flows into the collection chamber portion 70, the closing cap 28 provided at an outer periphery of the collection tube portion 46 is removed to allow the solution containing the nucleic acid to be extracted from the pre-treatment kit 42. Subsequently, the push mechanism 86 is activated to allow the push rod to squash the swollen portion forming the collection chamber portion 70 as depicted by arrow P3 in FIG. 18. Therefore, the collection chamber portion 70 is pressed to peel off the seal portion 20-3, allowing the solution in the collection chamber portion 70 to be fed into an external container (not depicted in the drawings) via the collection passage 72 (S16). The extraction treatment is then ended (S18). In the external container, a step for nucleic acid amplification and nucleic acid detection is executed by way of example.

The above-described closed type pre-treatment kit 42 enables automation of the process from lysis of the biological tissue through extraction of the nucleic acid and also allows prevention of contamination of the external environment. In particular, the closed type pre-treatment kit 42 is of a disposable type and can be disposed of without the need for special treatment, facilitating prevention of contamination of the external environment. Furthermore, the pre-treatment kit 42 adopts the seal structure which is simple but which allows the seal to be reliably peeled off in one direction to provide a communication passage. This enables the nucleic acid to be reliably extracted and purified while preventing contamination of the external environment.

Another Embodiment of the Pre-treatment Kit

FIG. 19 depicts a pre-treatment kit configured to extract nucleic acid from a biological tissue according to another embodiment. In the pre-treatment kit depicted in FIG. 11, the lysis chamber portion 44, the treatment liquid storage portion 46, the purifying chamber portion 48, and the collection chamber portion 70 are arranged in series from the upstream side toward the downstream side. However, in the pre-treatment kit depicted in FIG. 19, the upstream side of the collection chamber portion 70 branches into passages 54-1 and 54-2 such that the treatment liquid storage portion 46 and the purifying chamber portion 48 are coupled in parallel to the collection chamber portion 70 via the passages 54-1 and 54-2, respectively. The lysis chamber portion 44 is coupled to the upstream side of the purifying chamber portion 48 via the passage 52. The upstream side of the treatment liquid storage portion 46 is closed. The deformed portion 44B of the lysis chamber portion 44 and the deformed portion 46B of the treatment liquid storage portion 46 are provided with the band-like seal portions (peelable portions) 20-1 and 20-2, respectively.

In the pre-treatment kit with the compartments arranged as described above, the solution in the lysis chamber portion 44 and the treatment liquid in the treatment liquid storage portion 46, for example, an additive solution, can be separately and independently fed to the purifying chamber portion 48 and the collection chamber portion 70 by pushing the lysis chamber portion 44 and the treatment liquid storage portion 46 separately and independently. Thus, a complicated treatment or reaction can be easily achieved. Even if feeding of liquid from the lysis chamber portion 44 to the collection chamber portion 70 temporarily or steadily increases an internal pressure in the collection chamber portion 70, the seal portion (peelable portion) 20-2 between the treatment liquid storage portion 46 and the collection chamber portion 70 is difficult to peel off and release from the collection chamber portion 70 side. The additive solution serving as a treatment liquid can be fed to the collection chamber portion 70 by pressing the treatment liquid storage portion 46 at any timing.

Embodiment of a Biological and Chemical Treatment Kit

FIG. 20 depicts a biological and chemical treatment kit according to yet another embodiment. A biological and chemical treatment kit 110 comprises a plurality of compartment portions 102, 103, 104, 106 coupled to a reaction chamber portion 112 via passages 114, 116, 118, 120. In the compartment portions 102, 103, 104, 106, seal portions (peelable portions) 20-4, 20-5, 20-6, 20-7 defining the compartment portions 102, 103, 104, 106, respectively, are formed. Like the seal portion 20-1, the seal portions (peelable portions) 20-4, 20-5, 20-6, 20-7 are structured to be inhibited from being easily released by an increase in pressure on the passage 114, 116, 118, 120 sides, respectively, and to be relatively easily peeled off and released by an increase in internal pressure in the compartment portions 102, 103, 104, 106, respectively.

In the biological and chemical treatment kit, various reaction solutions, additive solutions, cleaning solutions, specimen solutions, and the like are fed into the compartment portions 102, 103, 104, 106 for storage through respective feeding ports not depicted in the drawings. Then, the compartment portions 102, 103, 104, 106 are pushed to peel off the seal portions (peelable portions) 20-4, 20-5, 20-6, 20-7. Therefore, in the biological and chemical treatment kit, various reaction solutions, additive solutions, cleaning solutions, specimen solutions, and the like can be fed into the reaction chamber portion 112 in any order so as to mix or react with one another. The present embodiment also allows restriction of peel-off of the seal portions (peelable portions) 20-4, 20-5, 20-6, 20-7 resulting from an increase in the pressure in the reaction chamber portion 112.

(Comparison Between a Comparative Example and the Ninth and Tenth Embodiments

Figure 21:
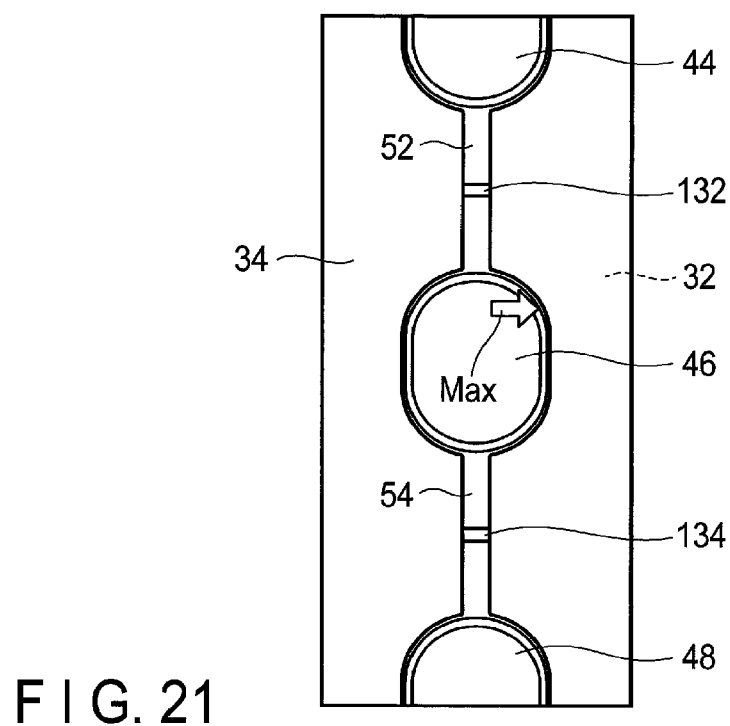
FIG. 21 is a front view schematically depicting a structure of a sealed chemical container according to a comparative example.
Figure 22:
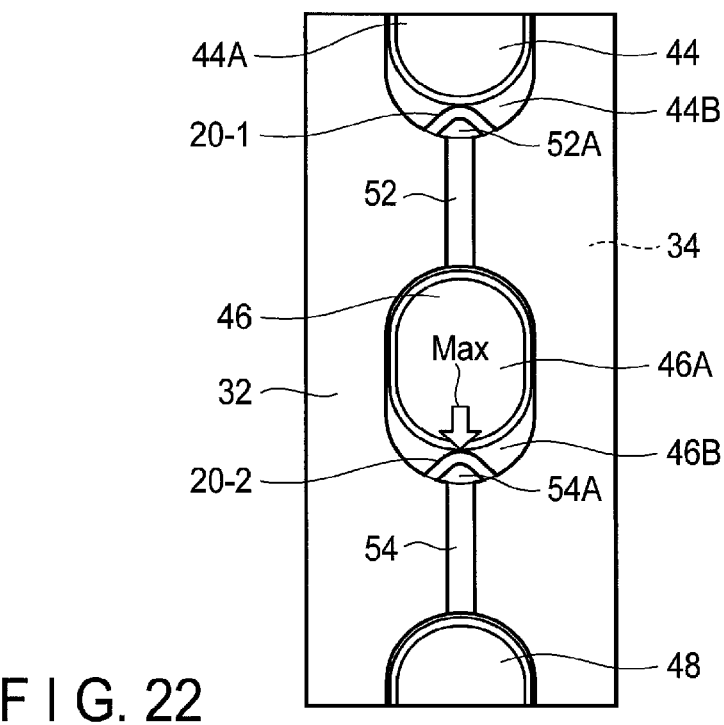
FIG. 22 is a front view schematically depicting a structure of a sealed chemical container according to a ninth embodiment.
Figure 23:
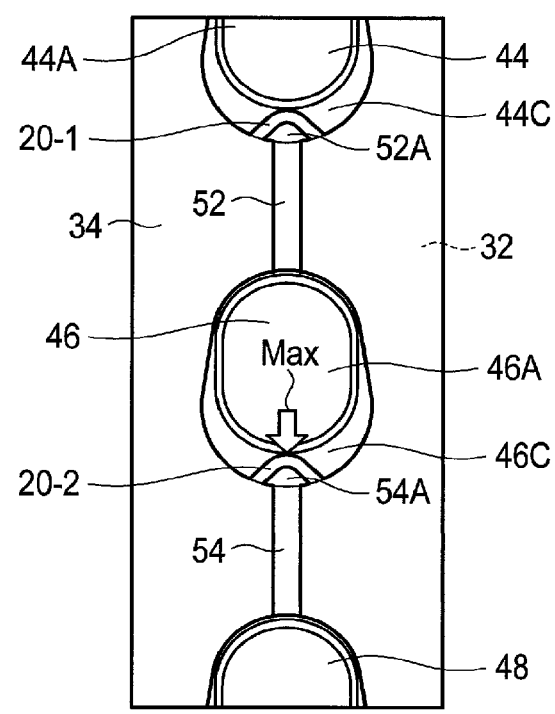
FIG. 23 is a front view schematically depicting a structure of a sealed chemical container according to a tenth embodiment.

FIG. 21 depicts a part of a pre-treatment kit according to a comparative example. FIG. 22 and FIG. 23 depict parts of pre-treatment kits according to the ninth and tenth embodiments. Each of the pre-treatment kits comprises compartment portions 44, 46, 48 each formed like a swollen semi-cylindrical shape having opposing end portions which are rounded. In the pre-treatment kit according to the comparative example depicted in FIG. 21, seal portions (peelable portions) 132, 134 are provided which linearly traverse the passage 53 coupling the compartment portions 44, 46 together and the passage 54 coupling the compartment portions 46, 48 together, respectively. In contrast, in the pre-treatment kit according to the ninth embodiment depicted in FIG. 22, each of the compartment portions 44, 46 is formed as the swollen semi-cylindrical shape which has the opposing end portions which are rounded. The compartment portions 44, 46 are provided with deformed portions 44B, 46B at the downstream side, respective. The deformed portions 44B, 46B are formed by collapsing each of the compartment portions 44, 46 into a circular arc shape. The band-like seal portions (peelable portions) 20-1, 20-2 extend into the deformed portions 44B, 46B so as to close the openings of the passages 52, 54. In the pre-treatment kit according to the tenth embodiment depicted in FIG. 23, each of the compartment portions 44, 46 is also formed as the swollen semi-cylindrical shape which has the opposing end portions which are rounded. The compartment portions 44, 46 are also provided with deformed portions 44B, 463 at the downstream side, respectively. The deformed portions 44B, 46B are formed by collapsing each of the compartment portions 44, 46 into a deformed crescent shape which is extended and expanded in the down stream side. The band-like seal portions 20-1, 20-2 also extend into the eggplant-shaped deformed portions 44B, 46B so as to close the openings of the passages 52, 54. The deformed crescent shape portions 44B, 46B depicted in FIG. 23 each have a larger area than each of the circular-arc-shaped deformed portions 44B, 46B depicted in FIG. 22. The passage 54 has a passage width gradually increasing toward the compartment on the upstream side, and the band-like seal portion 20-2 is arranged so as to close the passage opening with the increased width. Therefore, a higher stress is exerted on a protruding portion of the band-like seal portion 20-2 depicted in FIG. 23 than on a protruding portion of the band-like seal portion 20-2 depicted in FIG. 22.

As is the case with the above-described embodiments, the compartment portions 44, 46, 48 and the passages 52, 54 are defined by the primary seals, and the band-like seal portions 20-1, 20-2, 132, 134 are fused to the plate 32 with the secondary seals in a peelable manner.

A table illustrated in FIG. 24 indicates results of simulation of a structural analysis model in which the compartment portion 46 is pressed to increase the pressure in the compartment portion to stress the compartment portion 46. The table indicates a comparison of equivalent stress acting on the sheet 34 between numerical analysis models for the comparative example and the ninth and tenth embodiments which simulate a sheet with compartments formed therein. The table indicates the relation between a sheet thickness and the equivalent stress [MPa] and a stress ratio [%]. A secondary seal section of the table represents the equivalent stress [MPa] applied to the band-like seal portion 20-2 of the deformed portion 44B. A MAX section of the table represents the value of the maximum equivalent pressing force applied to the compartment portion 46. The maximum equivalent pushing force corresponds to the value of stress on an area denoted by arrow Max in FIG. 21 and FIG. 22. The stress ratio is defined as the ratio of the maximum equivalent stress Max to the equivalent stress on the secondary seal, and a larger value of the stress ratio indicates a structure in which the band-like seal portion 20-1, 20-2, 132, 134 forming the secondary seal is more easily peeled off without breaking the primary seal.

Conditions for the numerical analysis model are set as follows.

The sheet 34 is a numerical analysis model formed of polypropylene. Therefore, a longitudinal elastic modulus used in this case is a numerical value for polypropylene as a typical thermoplastic resin. The sheet 34 is set to have dimensions including a width of 20 mm, a length (height) of 50 mm, and a thickness of 0.15 mm. The size of the compartment portion 46 is set such that the compartment portion 46 is shaped like a generally semi-cylindrical shape which is 10 mm in width, 14 mm in length (height), and 5 mm in thickness and which has rounded opposite ends and that semicircular portions at the opposite ends are each shaped like a hemisphere having a circular art with a radius (R) of 5 mm. The passages 52, 54 have a width of 2 mm. The blocking portions (band-like portions) of the band-like seal portions 20-1, 20-2, 132, 134 have a width set to 1 mm along a direction in which the solution flows (an upstream to downstream direction). Boundary conditions are assumed to be such that the seal portions (primary seal portions) around the swollen portions and the band-like seal portions (secondary seal portions) 20-1, 20-2 are fixed onto the plate 32 and the internal pressure of the central compartment 46 in the swollen portion is 50 kPa and acts in directions in which the swollen portion is pushed open.

In the table illustrated in FIG. 24, the equivalent stress on the secondary seal indicates the stress values for the band-like seal portions 20-2, 134 functioning as downstream side blocking portions, and a larger numerical value of the equivalent stress indicates that the blocking portion is more easily peeled off. In the analysis model depicted in FIG. 21, the equivalent stress on the secondary seal is 0.53 MPa and the stress ratio is 4.00%. This indicates that substantially no stress is exerted, making peel-off difficult. In contrast, in the analysis model depicted in FIG. 22, the equivalent stress on the secondary seal is 10.6 MPa, which is approximately 20 times higher than the equivalent stress in the analysis model depicted in FIG. 21, and the stress ratio is 59.20%, indicating that this model corresponds to a structure with easier peel-off. In the analysis model depicted in FIG. 23, the equivalent stress on the secondary seal is 14.7 MPa and the stress ratio is 61.30%, indicating that, compared to the analysis model depicted in FIG. 22, the model depicted in FIG. 23 enables the peel-off to be more easily achieved due to an increased width (sealed opening width) of the passage on the upstream side of the blocking portion. In all of the analysis models, the upstream side blocking portion has a small stress value of 1 MPa or less, indicating difficult peel-off. The above-described results indicate that, in the closed container according to the embodiment, the blocking portion in any direction can be easily opened by a simple operation of pressing the compartment 46.

As described above, the testing container of the present embodiment has a simple container structure but allows the content of the container to be moved between the compartments using an easy method, enabling provision of a testing sealed chemical container and a testing apparatus for which cost reduction is possible.

In view of the above-described problems, an object of the embodiments of the present invention is to provide a low-cost sealed chemical container having a simple container structure but allowing the solution to be easily moved from the compartment in the container. Another object is to provide a pre-treatment kit and a nucleic acid extraction method for extracting nucleic acid from a biological tissue utilizing the sealed chemical container.

While certain embodiments have been described, these embodiments have been presented by way of example inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A chemical container comprising:
   a plate;
   a flexible sheet-like member including a bonding area fixedly bonded to the plate, the bonding area defining (1) a first compartment and (2) an outflow passage communicating with the first compartment via an opening of the first compartment; and
   a first seal portion located in the first compartment and manufactured to be weakly bonded to the plate compared to the bonding area so as to initially close the opening using the sheet-like member, the first seal portion defining an area protruding from the opening toward the first compartment, and the first seal portion blocking communication between (a) the first compartment and (b) the outflow passage when the first seal portion is weakly bonded to the plate,
   wherein the first seal portion is operable to peel off from the plate by an increase in an internal pressure of the first compartment that deforms the first compartment, and
   wherein a second passage is defined by a bonding area where the sheet-like member is fixedly bonded onto the plate so as to communicate with the first compartment,
   the chemical container further comprising:
   a feeding port portion through which a content is fed to the first compartment via the second passage;
   a first closing cap configured to close the feeding port portion in an openable manner;

a discharge port portion configured to communicate with the second passage to discharge the content in the first compartment; and
a second closing cap configured to close the discharge port portion in an openable manner,
wherein the first and second closing caps close the feeding port portion and the discharge port portion to close a container space comprising the first and second passages.

2. A testing apparatus comprising:
a closed chemical container including:
   a plate;
   a flexible sheet-like member including a bonding area fixedly bonded to the plate, the bonding area defining (1) a first compartment and (2) an outflow passage communicating with the first compartment via an opening of the first compartment; and
   a first seal portion located in the first compartment and weakly bonded to the plate compared to the bonding area so as to close the opening using the sheet-like member, the first seal portion defining an area protruding from the opening toward the first compartment, and the first seal portion blocking communication between (a) the first compartment and (b) the outflow passage,
   wherein the first seal portion is operable to peel off from the plate by an increase in an internal pressure of the first compartment that deforms the first compartment;
a push mechanism on which the closed chemical container is installed, to externally press the first compartment; and
a controller configured to activate the push mechanism to provide the increase in the internal pressure in the first compartment that is operable to peel off the first seal portion from the plate, allowing a content in the first compartment to be fed to the first passage.

3. A nucleic acid extraction container comprising:
a plate;
a flexible sheet-like member comprising a bonding area fixedly bonded onto the plate;
a first compartment defined and formed on the plate by the bonding area and enabled to receive a biological tissue and a solution to be externally fed into the first compartment;
a second compartment defined and formed on the plate by the bonding area and in which an adsorbent is located;
a third compartment defined and formed on the plate by the bonding area so as to lie between the first and second compartments and in which a first solution with which the adsorbent is wetted to activate an adsorption effect of the adsorbent is received;
a first passage which opens into the third compartment and which is defined by the bonding area so as to communicate with the first compartment via a first opening;
a second passage which opens into the second compartment and which is defined by the bonding area so as to communicate with the third compartment via a second opening;
a first seal portion (a) manufactured to be weakly bonded to the plate compared to the bonding area so as, when the first seal portion is weakly bonded to the plate, to initially close the first opening and block communication between the first compartment and the first passage and (b) operable to allow communication between the first compartment and the first passage after a first increase in internal pressure to the container; and
a second seal portion (a) manufactured to be weakly bonded to the plate compared to the bonding area so as, when the second seal portion is weakly bonded to the plate, to initially close the second opening and block communication between the second compartment and the second passage and (b) operable to allow communication between the second compartment and the second passage after a second increase in internal pressure to the container.

4. The nucleic acid extraction container of claim 3, wherein
the first compartment comprises a first area to which external pressure is to be applied to provide the first increase in the internal pressure and a second area that deforms in response to the first increase in the internal pressure while the first compartment remains fixedly bonded with the plate, and
the third compartment comprises a third area that deforms in response to a third increase in the internal pressure while the third compartment remains fixedly bonded with the plate.

5. The nucleic acid extraction container of claim 3,
wherein the first seal portion is formed like a band and comprises opposite ends ending at opposite sides of the first opening; and
wherein the second seal portion is formed like a band and comprises opposite ends ending at opposite sides of the second opening.

6. The nucleic acid extraction container of claim 3, further comprising:
a third passage is defined and formed on the plate by the bonding area so as to communicate with the first compartment;
a feeding port portion through which a biological tissue and a solution are fed into the first compartment via the third passage;
a first closing cap configured to close the feeding port portion in an openable manner;
a discharge port portion configured to communicate with the second compartment to discharge a discharge solution in the second compartment to an outside of the second compartment; and
a second closing cap configured to close the discharge port portion in an openable manner,
wherein the first and second closing caps close the feeding port portion and the discharge port portion to close an intra-container space comprising the first, second, and third passages.

7. A nucleic acid extraction apparatus comprising:
a nucleic acid extraction container comprising:
   a plate;
   a flexible sheet-like member comprising a bonding area fixedly bonded onto the plate;
   a first compartment defined and formed on the plate by the bonding area in which a biological tissue and a solution are housed;
   a second compartment defined and formed on the plate by the bonding area and in which an adsorbent is housed;
   a third compartment defined and formed on the plate by the bonding area so as to lie between the first and second compartments and in which a second solution with which the adsorbent is wetted to activate an adsorption effect of the adsorbent is housed;

a first passage which opens into the third compartment and which is defined by the bonding area so as to communicate with the first compartment via a first opening;

a second passage which opens into the second compartment and which is defined by the bonding area so as to communicate with the third compartment via a second opening;

a first seal portion (a) manufactured to be weakly bonded to the plate compared to the bonding area so as, when the first seal portion is weakly bonded to the plate, to initially close the first opening-and block communication between the first compartment and the first passage and (b) operable to allow communication between the first compartment and the first passage after a first increase in internal pressure to the container;

a second seal portion (a) manufactured to be weakly bonded to the plate compared to the bonding area so as, when the second seal portion is weakly bonded to the plate, to initially close the second opening and block communication between the second compartment and the second passage and (b) operable to allow communication between the second compartment and the second passage after a second increase in internal pressure to the container;

first and second push mechanisms on which the nucleic acid extraction container is installed, to externally and individually press the first and third compartments, respectively; and a controller configured to (a) activate the second push mechanism to provide the second increase in the internal pressure in the third compartment to peel off the second seal portion from the plate so that a second solution in the third compartment is fed to the second compartment via the second passage to wet the adsorbent with the second solution to activate an adsorption effect of the adsorbent and (b) activate the first push mechanism to provide the first increase in the internal pressure in the first compartment to peel off the first seal portion from the plate so that a first solution in the first compartment in which nucleic acid in the biological tissue and contaminants have been subjected to lysis is fed to the second compartment via the first passage, the third compartment, and the second passage, allowing the adsorbent to adsorb the contaminants to purify the first solution in which the nucleic acid has been subjected to lysis, the purified first solution being discharged.

8. A method of extracting nucleic acid utilizing a nucleic acid extraction container comprising:

a plate;

a flexible sheet-like member comprising a bonding area fixedly bonded onto the plate;

a first compartment defined and formed on the plate by the bonding area and enabled to receive a biological tissue and a solution to be fed into the first compartment;

a second compartment defined and formed on the plate by the bonding area and in which an adsorbent is located;

a third compartment defined and formed on the plate by the bonding area so as to lie between the first and second compartments and in which a second solution with which the adsorbent is wetted to activate an adsorption effect of the adsorbent is housed;

a first passage which opens into the third compartment and which is defined by the bonding area so as to communicate with the first compartment via a first opening;

a second passage which opens into the second compartment and which is defined by the bonding area so as to communicate with the third compartment via a second opening;

a first seal portion (a) manufactured to be weakly bonded to the plate compared to the bonding area so as, when the first seal portion is weakly bonded to the plate, to initially close the first opening and block communication between the first compartment and the first passage and (b) operable to allow communication between the first compartment and the first passage after a first increase in internal pressure to the container; and a second seal portion (a) manufactured to be weakly bonded to the plate compared to the bonding area so as, when the second seal portion is weakly bonded to the plate, to initially close the second opening and block communication between the second compartment and the second passage and (b) operable to allow communication between the second compartment and the second passage after a second increase in internal pressure to the container, the method comprising:

externally pressing the third compartment to provide the second increase in the internal pressure in the third compartment to peel off the second seal portion from the plate so that a second solution in the third compartment is fed to the second compartment via the second passage to wet the adsorbent with the second solution to activate an adsorption effect of the adsorbent; and pressing the first compartment to provide the first increase in the internal pressure in the first compartment to peel off the first seal portion from the plate so that a first solution in the first compartment in which nucleic acid in the biological tissue and contaminants have been subjected to lysis is fed to the second compartment via the first passage, the third compartment, and the second passage, allowing the adsorbent to adsorb the contaminants to purify the first solution in which the nucleic acid has been subjected to lysis, and discharging the purified first solution.

9. A chemical container comprising:

a plate;

a flexible sheet-like member including a bonding area fixedly bonded to the plate, the bonding area defining (1) a first compartment, (2) an outflow passage communicating with the first compartment via an opening of the first compartment, and (3) a second compartment; and a first seal portion located in the first compartment and manufactured to be weakly bonded to the plate compared to the bonding area so as to initially close the opening using the sheet-like member, the first seal portion defining an area protruding from the opening toward the first compartment, and the first seal portion blocking communication between (a) the first compartment and (b) the outflow passage and the second compartment when the first seal portion is initially weakly bonded to the plate, wherein the first seal portion is operable to peel off from the plate by an increase in an internal pressure of the first compartment that deforms the first compartment.

10. The chemical container of claim 9, wherein the opening is arranged on an upstream side of the outflow passage and has a width larger than a downstream side passage width of the outflow passage.

11. The chemical container of claim 9, wherein the first compartment comprises a first area to which external pressure is to be applied to provide the increase in the internal pressure of the first compartment and a second area that deforms in response to the increase in the internal pressure of the first compartment while the first compartment remains fixedly bonded with the plate.

12. The chemical container of claim 9, wherein the first seal portion is formed like a band and has opposite ends ending at opposite sides of the opening.

13. The chemical container of claim 9, wherein the first seal portion is formed like a band and comprises one or more sharp portions or rounded leading portions.

14. A chemical container comprising:
a plate;
a flexible sheet-like member including a bonding area fixedly bonded to the plate, the bonding area defining (1) a first compartment and (2) an outflow passage communicating with the first compartment via an opening of the first compartment; and
a first seal portion located in the first compartment and manufactured to be weakly bonded to the plate compared to the bonding area so as to initially close the opening using the sheet-like member, the first seal portion defining an area protruding from the opening toward the first compartment, and the first seal portion blocking communication between (a) the first compartment and (b) the outflow passage when the first seal portion is initially weakly bonded to the plate,
wherein the first seal portion is operable to peel off from the plate by an increase in an internal pressure of the first compartment that deforms the first compartment, and
wherein the opening is arranged on an upstream side of the outflow passage and has a width larger than a downstream side passage width of the outflow passage.

15. The chemical container of claim 14, further comprising a second compartment formed on the plate by the bonding area where the sheet-like member is fixedly bonded onto the plate, the second compartment being deformable and communicating with the first compartment via the outflow passage.

16. The chemical container of claim 14, wherein the first compartment comprises a first area to which external pressure is to be applied to provide the increase in the internal pressure of the first compartment and a second area that deforms in response to the increase in the internal pressure of the first compartment while the first compartment remains fixedly bonded with the plate.

17. The chemical container of claim 14, wherein the first seal portion is formed like a band and has opposite ends ending at opposite sides of the opening.

18. The chemical container of claim 14, wherein the first seal portion is formed like a band and comprises one or more sharp portions or rounded leading portions.

19. A chemical container comprising:
a plate;
a flexible sheet-like member including a bonding area fixedly bonded to the plate, the bonding area defining (1) a first compartment and (2) an outflow passage communicating with the first compartment via an opening of the first compartment; and
a first seal portion located in the first compartment and manufactured to be weakly bonded to the plate compared to the bonding area so as to initially close the opening using the sheet-like member, the first seal portion defining an area protruding from the opening toward the first compartment, and the first seal portion blocking communication between (a) the first compartment and (b) the outflow passage when the first seal portion is initially weakly bonded to the plate,
wherein the first seal portion is operable to peel off from the plate by an increase in an internal pressure of the first compartment that deforms the first compartment, and
wherein the first compartment comprises a first area to which external pressure is to be applied to provide the increase in the internal pressure of the first compartment and a second area that deforms in response to the increase in the internal pressure of the first compartment while the first compartment remains fixedly bonded with the plate.

20. The chemical container of claim 19, further comprising a second compartment formed on the plate by the bonding area where the sheet-like member is fixedly bonded onto the plate, the second compartment being deformable and communicating with the first compartment via the outflow passage.

21. The chemical container of claim 19, wherein the opening is arranged on an upstream side of the outflow passage and has a width larger than a downstream side passage width of the outflow passage.

22. The chemical container of claim 19, wherein the first seal portion is formed like a band and has opposite ends ending at opposite sides of the opening.

23. The chemical container of claim 19, wherein the first seal portion is formed like a band and comprises one or more sharp portions or rounded leading portions.

24. A chemical container comprising:
a plate;
a flexible sheet-like member including a bonding area fixedly bonded to the plate, the bonding area defining (1) a first compartment and (2) an outflow passage communicating with the first compartment via an opening of the first compartment; and
a first seal portion located in the first compartment and manufactured to be weakly bonded to the plate compared to the bonding area so as to initially close the opening using the sheet-like member, the first seal portion defining an area protruding from the opening toward the first compartment, and the first seal portion blocking communication between (a) the first compartment and (b) the outflow passage when the first seal portion is initially weakly bonded to the plate,
wherein the first seal portion is operable to peel off from the plate by an increase in an internal pressure of the first compartment that deforms the first compartment, and
wherein the first seal portion is formed like a band and has opposite ends ending at opposite sides of the opening.

25. The chemical container of claim 24, further comprising a second compartment formed on the plate by the bonding area where the sheet-like member is fixedly bonded onto the plate, the second compartment being deformable and communicating with the first compartment via the outflow passage.

26. The chemical container of claim 24, wherein the opening is arranged on an upstream side of the outflow passage and has a width larger than a downstream side passage width of the outflow passage.

27. The chemical container of claim 24, wherein the first compartment comprises a first area to which external pressure is to be applied to provide the increase in the internal pressure of the first compartment and a second area that deforms in response to the increase in the internal pressure of the first compartment while the first compartment remains fixedly bonded with the plate.

28. The chemical container of claim 24, wherein the first seal portion further comprises one or more sharp portions or rounded leading portions.

* * * * *